(12) United States Patent
Siala et al.

(10) Patent No.: US 12,364,738 B2
(45) Date of Patent: Jul. 22, 2025

(54) COMPOSITION COMPRISING AT LEAST ONE ENZYME AND AT LEAST ONE MICROBICIDAL MOLECULE FOR THE PREVENTION OR TREATMENT OF POST-IMPLANT INFECTIONS

(71) Applicant: ONELIFE S.A., Louvain-la-Neuve (BE)

(72) Inventors: Wafi Siala, Woluwe St. Pierre (BE); Thomas Vanzieleghem, Louvain-la-Neuve (BE)

(73) Assignee: ONELIFE S.A., Louvain-la-Neuve (BE)

( * ) Notice: Subject to any disclaimer, the term of this patent is extended or adjusted under 35 U.S.C. 154(b) by 473 days.

(21) Appl. No.: 16/308,261

(22) PCT Filed: Jun. 2, 2017

(86) PCT No.: PCT/EP2017/063533
§ 371 (c)(1),
(2) Date: Dec. 7, 2018

(87) PCT Pub. No.: WO2017/211737
PCT Pub. Date: Dec. 14, 2017

(65) Prior Publication Data
US 2019/0192639 A1  Jun. 27, 2019

(30) Foreign Application Priority Data

Jun. 8, 2016 (BE) .................................. 2016/5427
Jun. 8, 2016 (EP) .................................. 16173468

(51) Int. Cl.
| | | |
|---|---|---|
| *A61K 38/46* | (2006.01) | |
| *A61K 9/00* | (2006.01) | |
| *A61K 9/08* | (2006.01) | |
| *A61K 9/19* | (2006.01) | |
| *A61K 31/407* | (2006.01) | |
| *A61K 31/4709* | (2006.01) | |
| *A61K 31/496* | (2006.01) | |
| *A61K 31/7036* | (2006.01) | |
| *A61K 38/43* | (2006.01) | |
| *A61K 38/47* | (2006.01) | |
| *A61K 45/06* | (2006.01) | |
| *A61L 27/54* | (2006.01) | |
| *A61L 29/16* | (2006.01) | |
| *A61L 31/16* | (2006.01) | |
| *A61P 31/04* | (2006.01) | |

(52) U.S. Cl.
CPC .......... *A61K 38/465* (2013.01); *A61K 9/0019* (2013.01); *A61K 9/08* (2013.01); *A61K 9/19* (2013.01); *A61K 31/407* (2013.01); *A61K 31/4709* (2013.01); *A61K 31/496* (2013.01); *A61K 31/7036* (2013.01); *A61K 38/43* (2013.01); *A61K 38/47* (2013.01); *A61K 45/06* (2013.01); *A61L 27/54* (2013.01); *A61L 29/16* (2013.01); *A61L 31/16* (2013.01); *A61P 31/04* (2018.01); *C12Y 301/21001* (2013.01); *C12Y 302/01004* (2013.01); *C12Y 302/01052* (2013.01); *A61L 2300/404* (2013.01); *Y02A 50/30* (2018.01)

(58) Field of Classification Search
CPC ...... A61K 38/465; A61K 9/0019; A61K 9/08; A61K 9/19; A61K 31/496; A61K 38/47; A61P 31/04; C12Y 301/21001; C12Y 302/01004; C12Y 302/01052
See application file for complete search history.

(56) References Cited

U.S. PATENT DOCUMENTS

| | | | |
|---|---|---|---|
| 10,039,812 B2* | 8/2018 | Dawson | A61P 31/04 |
| 2006/0246049 A1* | 11/2006 | Kaplan | C12Y 302/01052 424/94.61 |
| 2008/0019956 A1* | 1/2008 | Kumar | A01N 63/10 424/94.2 |
| 2008/0199509 A1* | 8/2008 | Nick | A61K 31/785 424/423 |
| 2009/0130082 A1* | 5/2009 | Kaplan | A61K 31/14 424/94.61 |
| 2009/0202516 A1* | 8/2009 | Olmstead | A61K 38/465 424/94.61 |
| 2011/0129454 A1* | 6/2011 | Olmstead | A61K 38/482 424/94.2 |
| 2013/0052250 A1* | 2/2013 | Burgess | A61K 45/06 424/411 |
| 2014/0356901 A1* | 12/2014 | Peppou | G01N 33/493 435/34 |

FOREIGN PATENT DOCUMENTS

WO       2009121183 A1    10/2009

OTHER PUBLICATIONS

Idowu et al., Antibiotics, 6(26):1-24 (2017) (Year: 2017).*
Merck Manuals,https://www.merckmanuals.com/professional/infectious-diseases/bacteria-and-antibacterial-drugs/fluoroquinolones, (Access Sep. 22, 2020) (Year: 2020).*
Moriarty et al., EFORT Open Rev., 1:89-99 (2016) (Year: 2016).*
Novozymes, Biocatalysis (2016) (Year: 2016).*
Kaplan et al., Antimicrob. Agents Chemother., 48(7):2633-2636 (2004) (Year: 2004).*
Medina et al., Res. Microbiol., 160:224-231 (2009) (Year: 2009).*

(Continued)

*Primary Examiner* — Kade Ariani
(74) *Attorney, Agent, or Firm* — Christensen O'Connor Johnson Kindness PLLC

(57) ABSTRACT

The present invention relates to a composition comprising at least one enzyme and at least one microbicidal molecule as combination products, for simultaneous use, separated use or use staggered over time, for use in the preventative and/or curative treatment of infections at an implant site, said infections being post-implant infections of mammalian bodies, in particular post-implant infections of the human body.

1 Claim, 15 Drawing Sheets

(56) References Cited

OTHER PUBLICATIONS

Kaplan et al., J Antibiot (Tokyo). Feb. 2012 ; 65(2): 73-77. doi:10.1038/ja.2011.113.*

Meng et al., Letters in Applied Microbiology, 2014, vol. 59, p. 306-312.*

Loiselle et al., The Journal of Bioadhesion and Biofilm Research, Biofouling, 2003, vol. 19, No. 2, p. 77-85.*

Izano et al., Applied and Environmental Microbiology, 2008, vol. 74, No. 2, p. 470-476.*

Baelo, A., et al., "Disassembling Bacterial Extracellular Matrix with DNase-coated Nanoparticles to Enhance Antibiotic Delivery in Biofilm Infections," Journal of Controlled Release, Apr. 23, 2015, pp. 150-158.

International Search Report mailed Sep. 22, 2017, issued in corresponding International Application No. PCT/EP2017/063533, filed Jun. 2, 2017, 4 pages.

Arciola, C.R., et al., "New Trends in Diagnosis and Control Strategies for Implant Infections," Editorial, 2011 The Authors—ISSN 0391-3988, Int J Artif Organs 2011; 34(9): pp. 727-736.

Cavaliere, R., et al., "The Biofilm Matrix Destabilizers, EDTA and DNaseI, Enhance the Susceptibility of Nontypeable Hemophilus Influenzae Biofilms to Treatment with Ampicilin and Ciprofloxacin," Original Research, 2014 The Authors, MicrobiologyOpen 2014; 3(4): pp. 557-567.

Kaplan, J.B., et al., "Recombinant human DNase 1 Decreases Biofilm and Increases Antimicrobial Susceptibility in Staphylococci," Original Article, The Journal of Antibiotics (2012) 65, pp. 73-77, 2012 Japan Antibiotics Research Association.

Tetz, G.V., et al., "Effect of DNase and Antibiotics on Biofilm Characteristics," Antimicrobial Agents and Chemotherapy, Mar. 2009, 53(3): pp. 1204-1209.

Kaplan, J.B., et al., "Extracellular DNA-dependent Biofilm Formation by *Staphylococcus epidermidis* RP62A in Response to Subminimal Inhibitory Concentrations of Antibiotics," Research in Microbiology 162 (2011) pp. 535-541.

Kaplan, J.B., "Therapeutic Potential of Biofilm-Dispersing Enzymes," The International Journal of Artificial Organs, 32 (9), 2009, pp. 545-554.

* cited by examiner

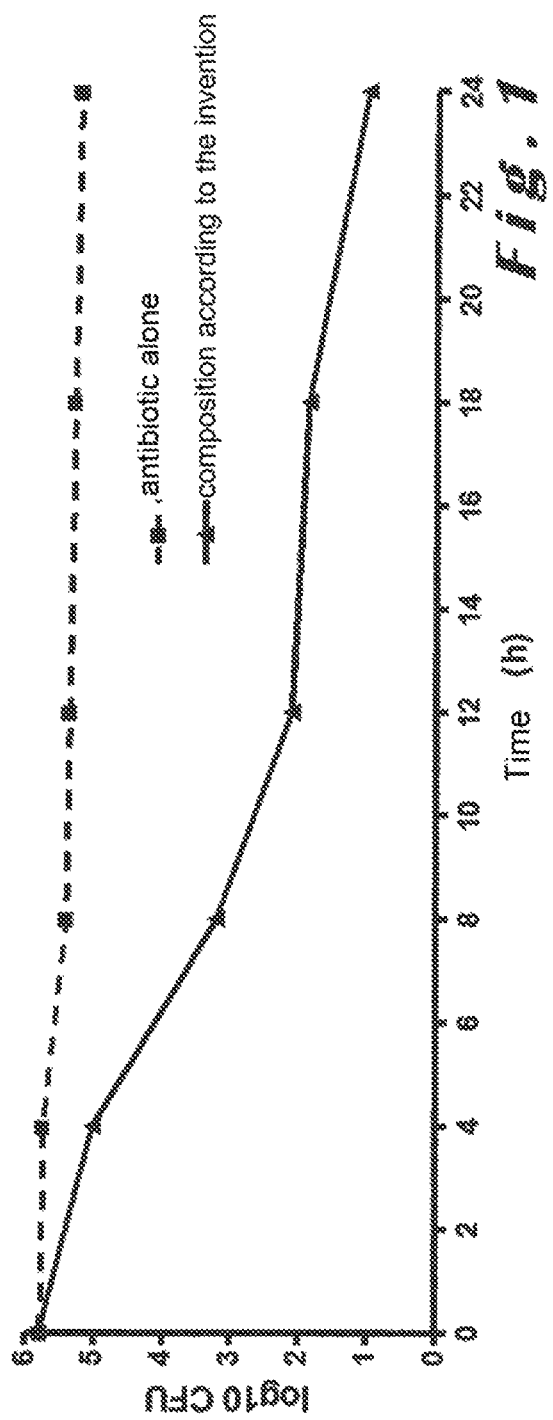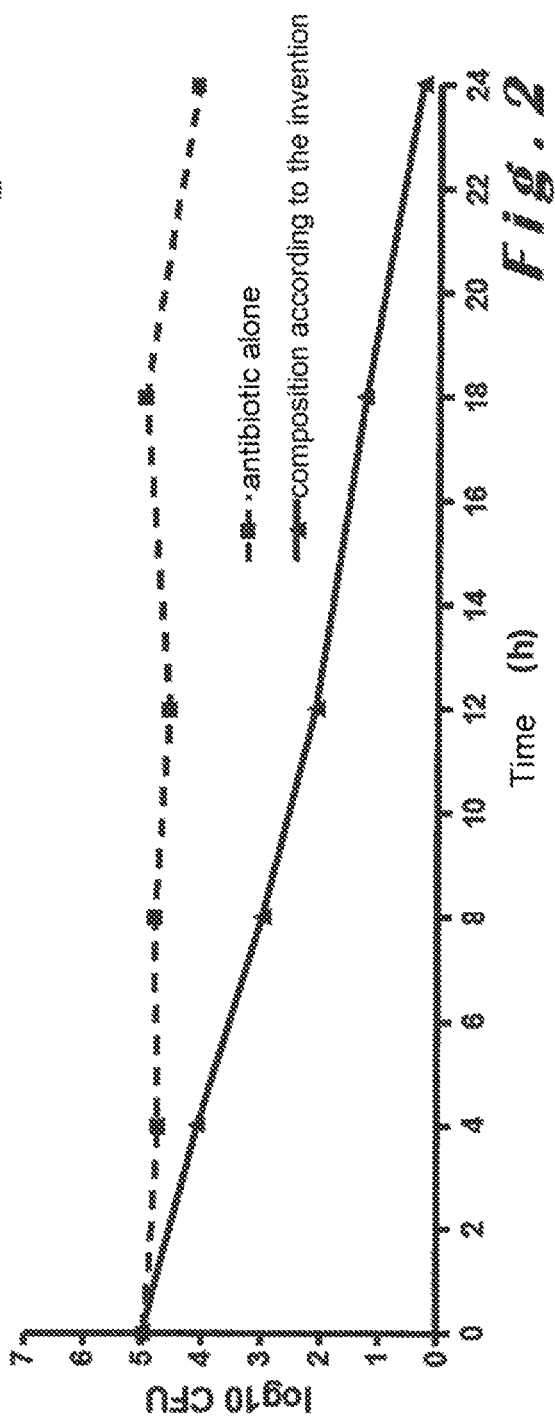

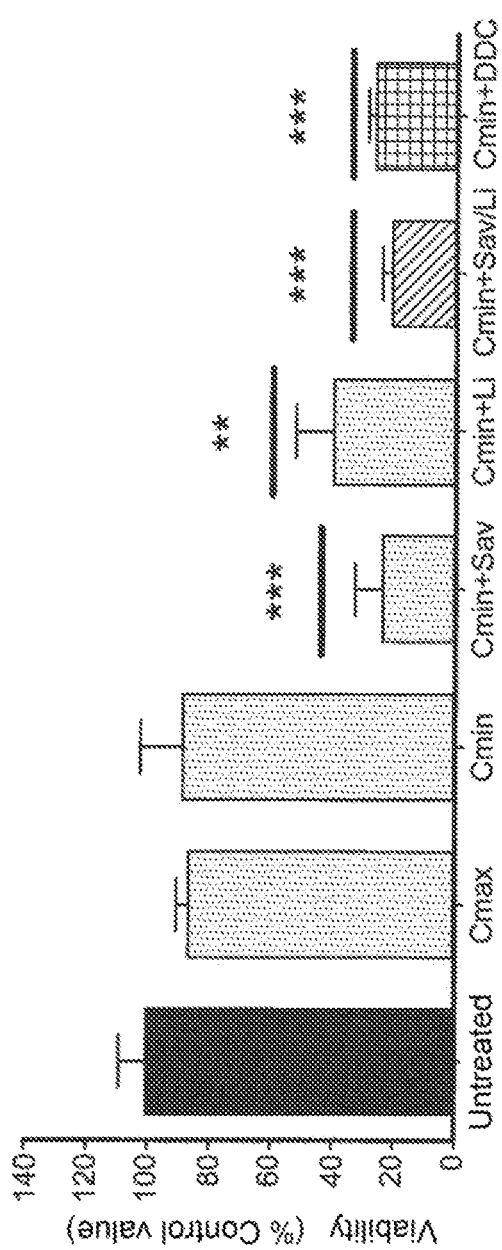
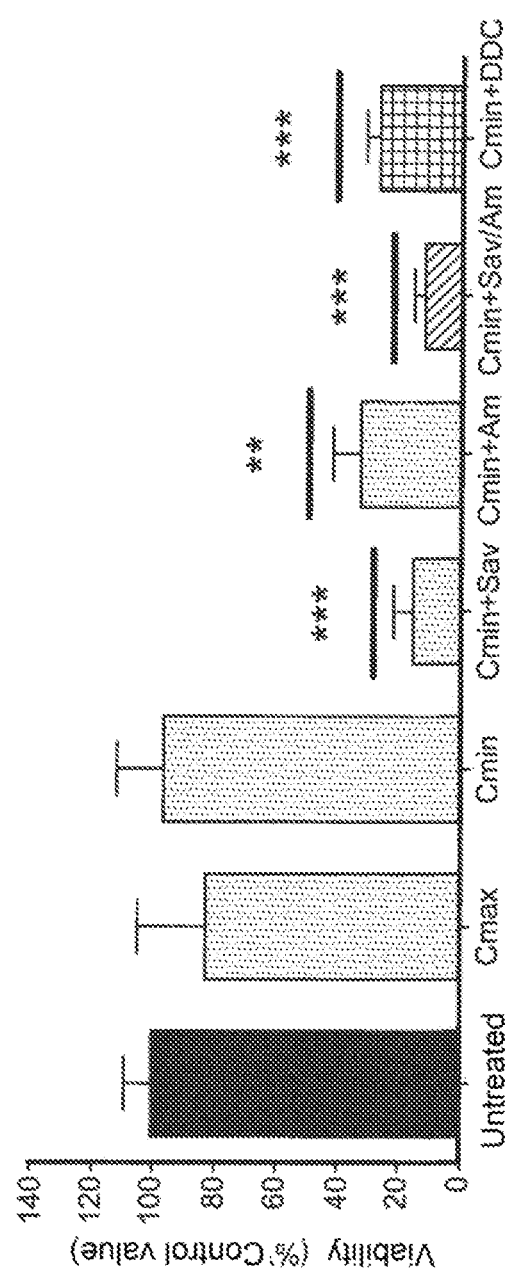

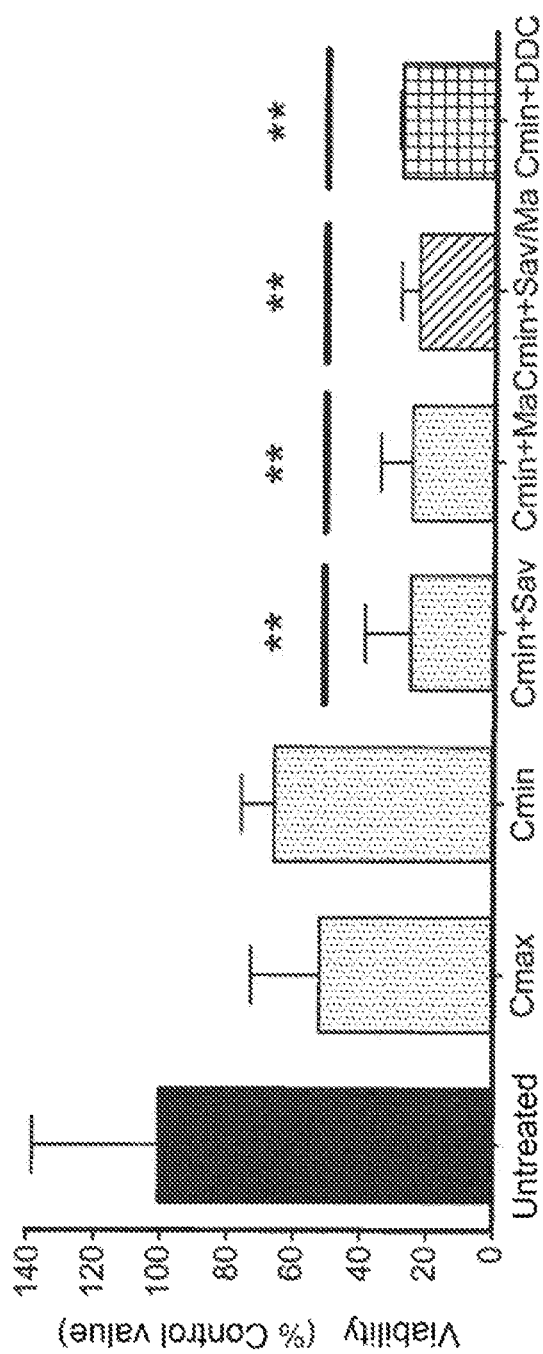
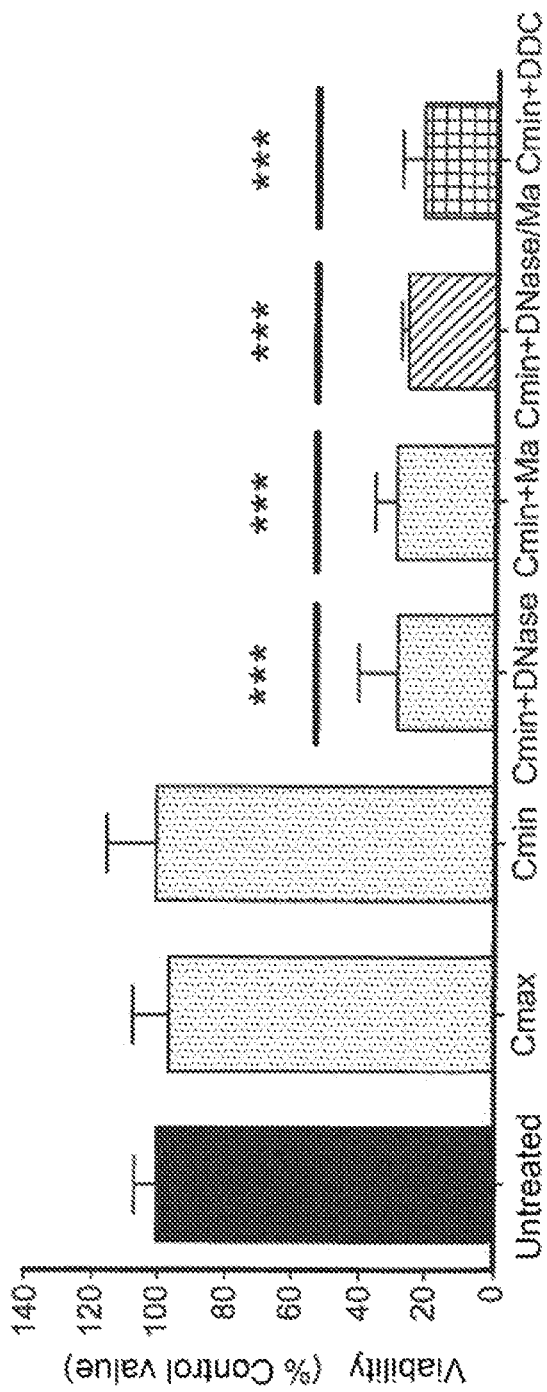
Fig. 7c
Fig. 7d

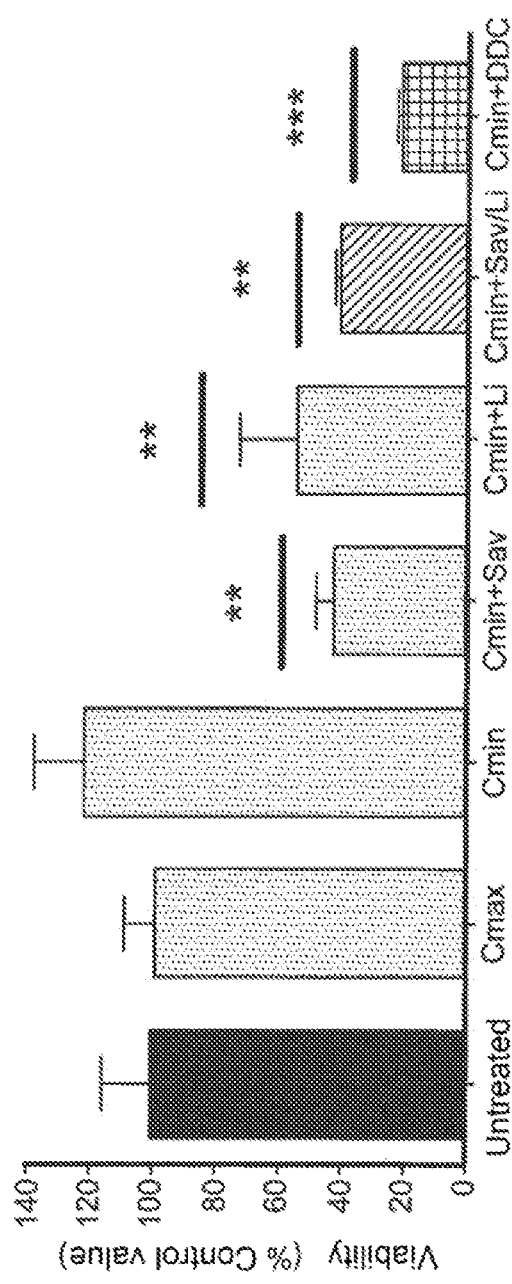
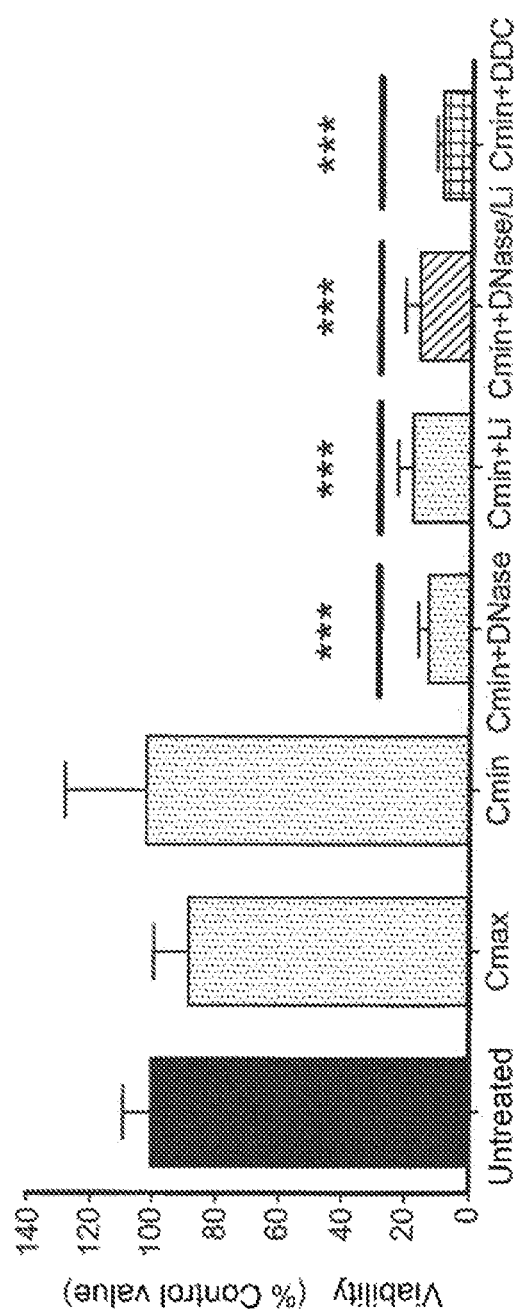

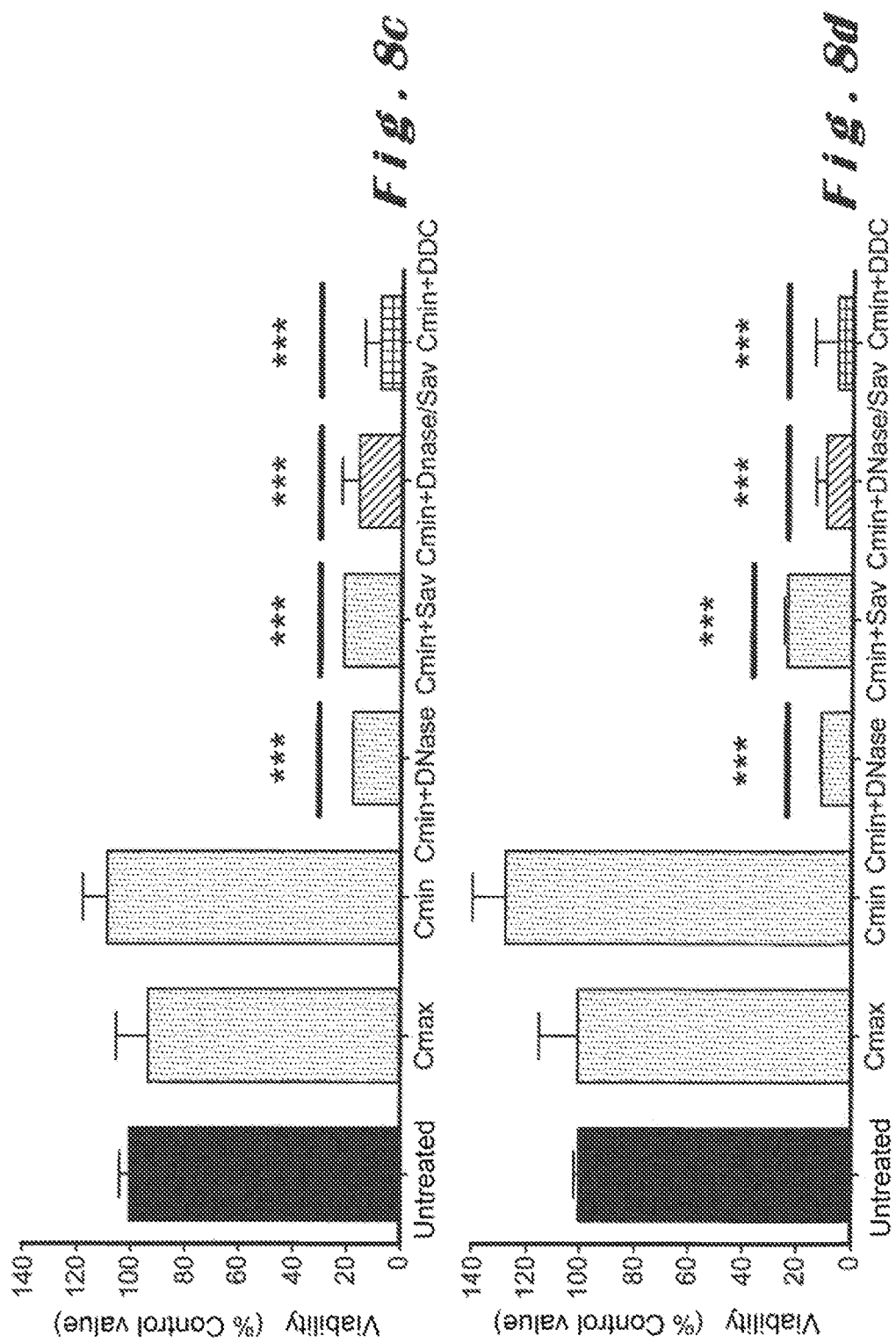

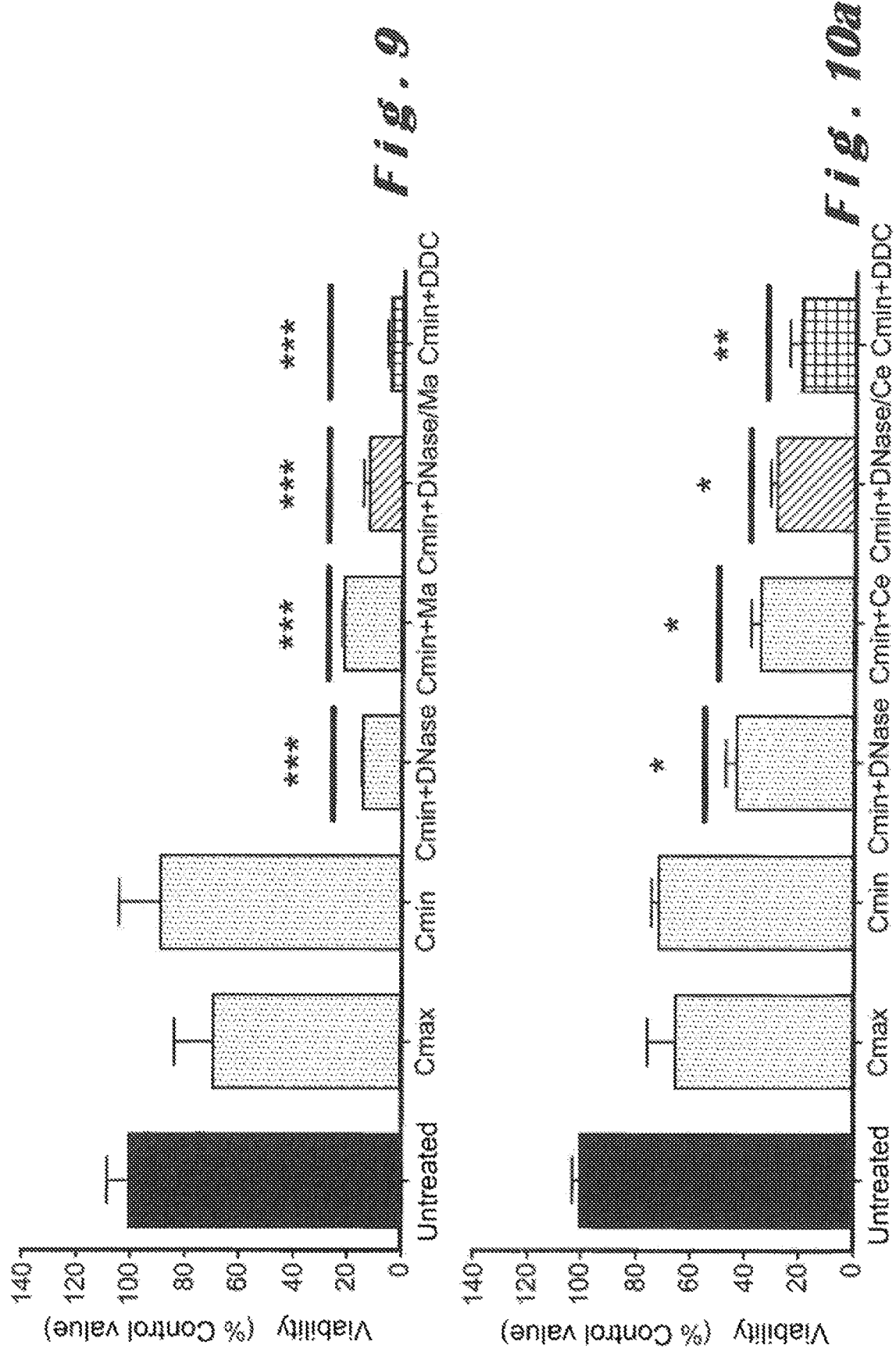

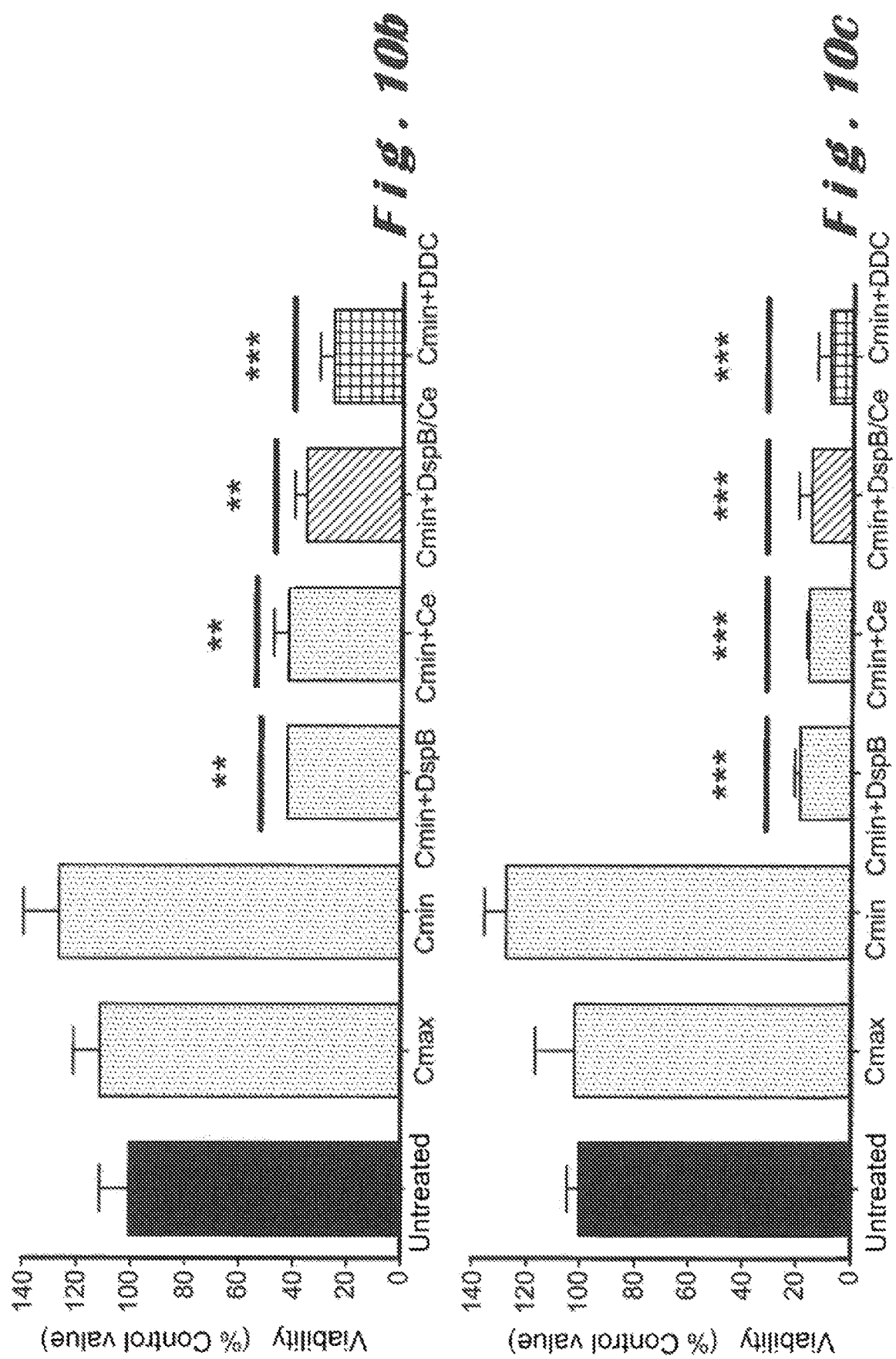

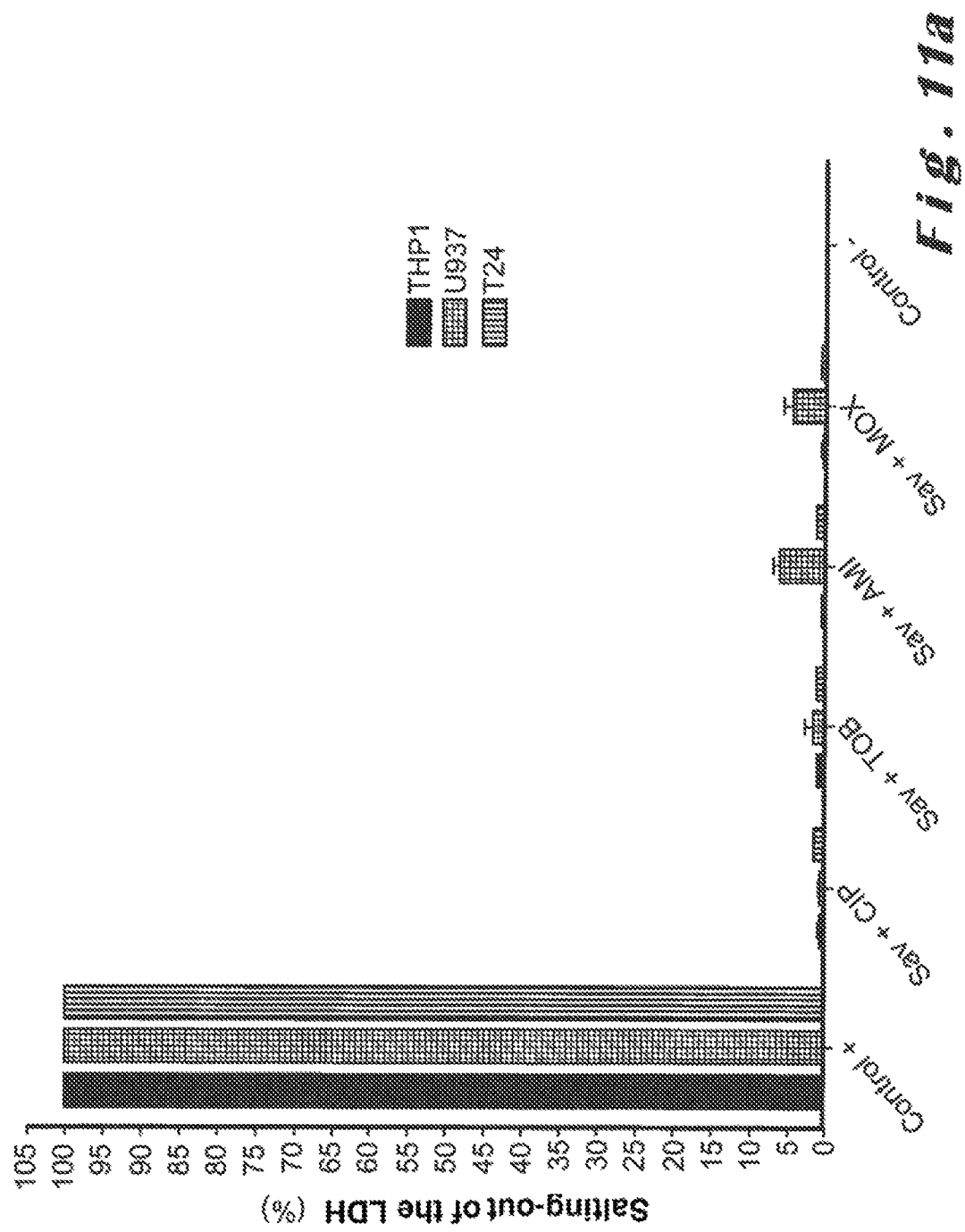

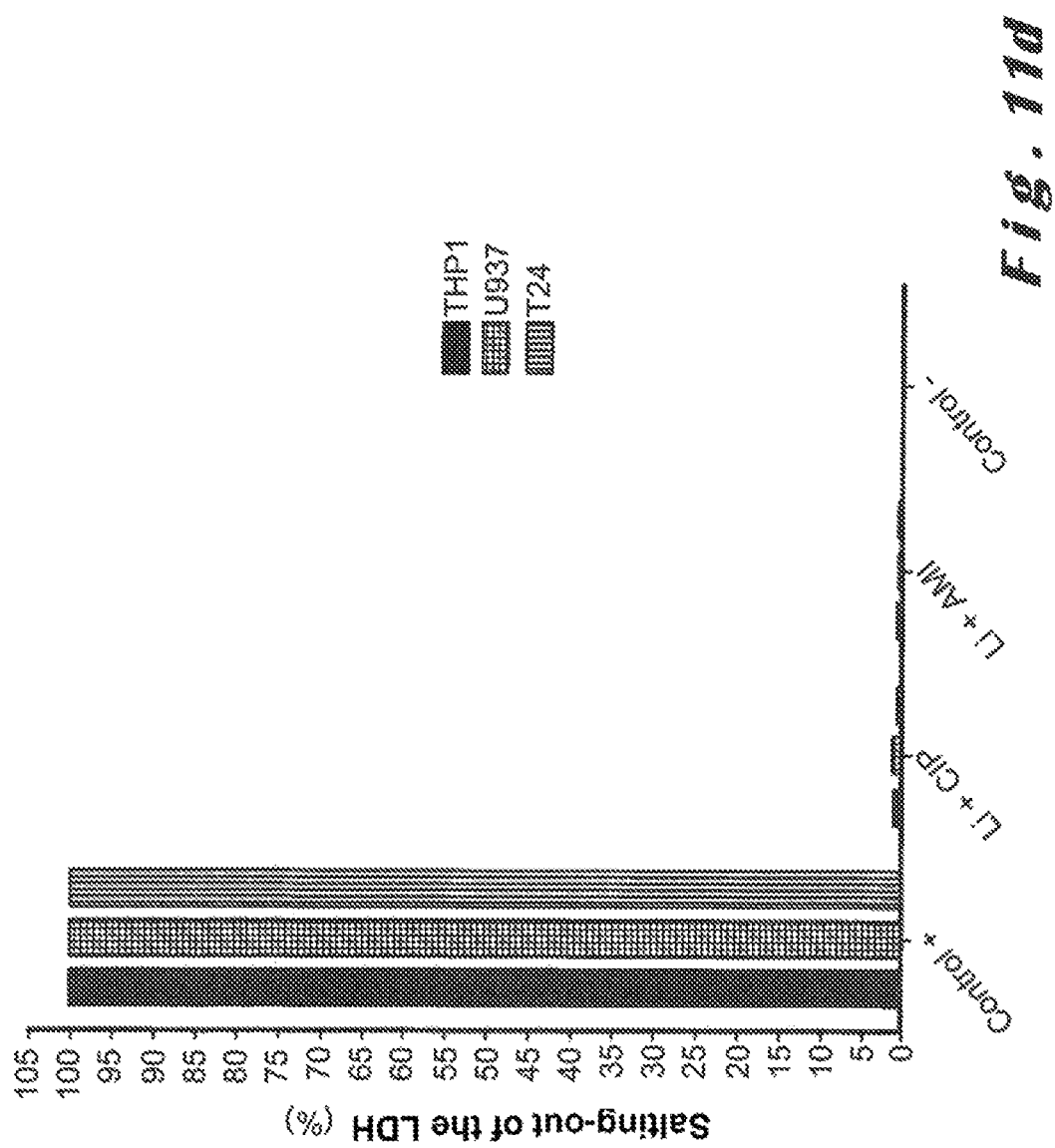

COMPOSITION COMPRISING AT LEAST ONE ENZYME AND AT LEAST ONE MICROBICIDAL MOLECULE FOR THE PREVENTION OR TREATMENT OF POST-IMPLANT INFECTIONS

The present invention relates to a composition comprising at least one enzyme and at least one microbicidal molecule, for use in the preventative and/or curative treatment of infections of mammalian bodies, in particular in the preventative and/or curative treatment of the human body.

One such composition is known from document WO2004/062677 which discloses a composition which must comprise a bacteriophage and an enzyme (polysaccharide lyase) and, optionally, an antimicrobial agent and/or a DNase, for treating biofilms and microbial illnesses (infections) associated with these biofilms. More particularly, this document describes use of such a composition in a method for treating pulmonary and gastro-intestinal infections related to the presence of biofilms.

Documents US2009/0130082 and WO2009/121183 describe compositions comprising a DNase for dispersing the biofilm and an antibiotic (antimicrobial agent) to kill the released bacteria. According to these prior documents, these compositions are especially used in the manufacturing/preparation of medical devices for treating wounds. To that end, the medical devices are coated or impregnated with a composition comprising a DNase and an antibiotic. More specifically, these prior documents essentially teach that such compositions are used for preparing medical devices and for disinfecting the skin or the surrounding environment before insertion or implantation of a medical device such as a catheter, for example. In this regard, the compositions disclosed in these prior documents are essentially used as pre-procedural rinsing solutions before surgery, for example.

A biofilm is a slime layer which grows on all surfaces, due to the adhesion of microorganisms on these surfaces and the secretion therefrom of polymers which coat them and facilitate their adhesion. The biofilms thus form a layer of protection around the microorganisms and represent a recurrent source of contamination of the surrounding environment which raises major problems in terms of health, for example in hospital environments.

More specifically, the accumulation of polymers secreted by the bacteria creates a matrix essentially composed of polysaccharides, DNA, proteins as well as lipids, which protects these microorganisms from external aggressions and are very resistant to conventional cleaning and disinfecting procedures. The microorganisms therefore thrive easily within this protective matrix and contaminate the surrounding environment by forming a particularly critical reservoir which is difficult to eliminate.

It is known that the problem of the presence of biofilms is twofold. Firstly, as indicated above, they represent a permanent source of contamination which is very difficult to eliminate by conventional means, even by the most aggressive means. Indeed, common disinfectants are often ineffective as it has been observed that they do not reach the microorganisms which are protected by the biofilm matrix composed of polysaccharides, DNA, proteins and lipids.

Secondly, a biofilm is mixed in that it is initially developed by certain bacterial strains, but it may accommodate others, these strains living and developing in colonies. However, these colonies promote communication between bacteria and, among other things, the exchange and spreading of resistance genes carried by certain bacteria. The biofilms formed by these gene exchanges are thus more difficult to eliminate and increasingly powerful means of disinfection or treatment must be resorted to, which, however, frequently encounter major problems of resistance and/or tolerance.

The protective matrix of the bacteria forming the biofilms is so resistant that it constitutes a real barrier protecting the bacteria from microbicidal agents (antibiotics and/or biocides) which could act against the microorganisms and thus against the infections related to the presence of biofilms, including infections of the human body associated with the presence of biofilm. Currently the common treatments based on different antibiotics and/or different biocides, even when they are, in certain cases, combined with other compounds (formulated and/or sequestering detergents and/or dispersants and/or surfactants), do not act in a sufficiently effective manner because they do not penetrate, or they do so only in a limited way, through the thickness of the biofilm. Furthermore, the microbicides may be inhibited by certain molecules forming this matrix. Consequently, the current treatments are only partially effective, only on the surface of the biofilm, the matrix of the biofilm effectively protecting the bacteria from dehydration phenomena, antibiotic and biocidal activity (and more generally microbicidal molecules), phagocytosis and acids. In that regard, it is generally accepted that biofilms are up to 1000 times more resistant to microbicides compared to planktonic bacteria (not protected by a biofilm).

In hospital and veterinary environments, the situation is all the more critical as numerous microorganisms responsible for the formation of biofilms are detected in numerous places, such as on individual patients/animals (wounds, respiratory system, etc.), in the surrounding area (operating room, surgical tools, equipment for maintaining said tools, endoscopes, urinary tubes, catheters, medical equipment, dialysis or assisted breathing machines for individuals, etc.) and on surfaces (floors, walls, operating tables, etc.).

From all of this, it appears that biofilms constitute a real problem, particularly in the fields of healthcare (hospitals, dental surgeries, etc.) and veterinary care. This problem is all the more critical as biofilms involve bacteria responsible for infections which could be fatal in individuals, for example among individuals developing an infection caused by *Staphylococcus* bacteria or Enterobacteriaceae which tend to be resistant to the most recent generation of antibiotics (for example, imipenem and carbapenems). It is therefore necessary to take all possible precautions in order to avoid the formation and development of biofilms; this is all the more important when interactions, that is to say surgical procedures, in mammalian bodies, in particular the human body, are carried out.

In that regard, the placing of medical devices in mammalian bodies, in particular in the human body (prostheses, implants—plates, screws, meshes, etc.—, catheters, urinary tubes, etc.), constitutes a critical medical procedure, these medical devices remain in place in the body for several days, or several months or years, following their placing. Indeed, as it concerns the implantation of a medical device in the body, this device almost inevitably constitutes a point of entry, vector potential and a potential source of microorganisms (including bacteria) capable of later developing biofilms within mammalian bodies, in particular within the human body, with all the risks involved.

The presence of bacteria on implantable medical devices, typically the presence of *Staphylococcus aureus* bacteria, *Staphylococcus epidermis* bacteria, *Klebsiella pneumoniae* bacteria, *Enterococcus faecalis* bacteria, *Escherichia coli* bacteria and *Pseudomonas aeruginosa* bacteria, or other mammalian pathogens, may have several origins, the main origins being contamination of the implantable medical device by contact with the skin of the individual (human/animal) during its implantation, contamination by microorganisms present in the air of the operating rooms and medical/veterinary practices or contamination by blood dispersion of bacteria from a secondary source.

Other origins of the presence of microorganisms on medical devices may be mentioned such as, for example, aerosol contamination (contaminants present in the air), aqueous contamination and contamination by contact with an already contaminated surface.

Generally, it is accepted that it is the so-called perioperative contaminations (which take place in the context of a medical procedure) which are the origin of the infections which develop following the placing of a medical device (implantation) in the mammalian body, in particular in the human body, this following the development of biofilms. For example, in catheters/urinary and blood tubes, perioperative contaminations are commonly observed as these medical devices are highly susceptible to contamination during their use, particularly considering the region of the body where they are implanted.

The adhesion of the biofilms may be promoted by implanted medical devices having rough portions where the shearing forces are lower and where the adhesion surfaces are greater. It also seems that hydrophobic surfaces promote the adhesion of biofilms to implanted medical devices. In addition, bodily fluids may constitute a surface coating on the medical devices which promote the adhesion of certain microbial species. For example, fibrinogen and collagen contribute to the adhesion of bacteria of the genus *Staphylococcus*.

Thus far, in order to better minimise any introduction of bacteria or other microorganisms (yeasts, moulds and viruses) within mammalian bodies, in particular in the human body, during the placing of an implantable medical device, a series of measures must be strictly observed. In that regard, the operators should exercise caution by disinfecting their hands and correctly disinfecting the skin of the human or animal individual at the site where the implantable medical device will be inserted. The operators must also ensure that the implantable medical devices are manipulated as little as possible during their placing, which requires a certain expertise. Furthermore, the sterility of the working environment must also be guaranteed, as well as the medical tools used in these procedures.

Other alternatives are currently available, such as, for example, the development of implantable medical devices whose design reduces the rates of infection. Implants with particular features are also envisaged in order to minimise the adherence surfaces, particularly by proposing hydrophilic or anionic surfaces or surfaces comprising a specific coating.

However, unfortunately, the development of post-implantation infections related to the development of biofilm in mammalian bodies is very frequently observed, in particular in the human body, these infections developing following the placing of a medical device which, even after having been subject to a potential pre-implantation treatment (sterilisation or recoating, for example), is regularly responsible for the contamination of internal tissues and/or mucosa in mammalian bodies, particularly in the human body. This tissue contamination is much faster and more damaging due to the trauma related to the surgical procedure of placing the implantable medical device, the immune defences of the human or animal individual may be (locally) weakened and thus enable easy development of acute infections.

Very often, occasionally alongside an acute inflammation, a so-called chronic infection is observed due to the implanted medical device not being clinically inert with regard to the surrounding tissues and/or the microorganisms found in and around the implanted medical device (that is at the implantation site of the implantable medical device). At this more advanced stage in the development of the inflammation, breakdown of the tissues (for example, bone tissue) may take place, which creates a preferential site where microorganisms may be better located and better develop in the form of biofilm, a site where the immune defences are locally weakened and thus a site where infections may appear and develop all the more easily. What is more, the inflammation may also be such that it prevents the implant from correctly integrating into mammalian bodies, in particular into the human body.

There follows, in mammalian bodies, in particular in the human body, the development of biofilms on both the implantable medical device itself as well as in the surrounding tissues, which may lead to situations which may require heavy antibiotic treatment. In extreme cases, new surgical procedures may have to be carried out in order to remove the implantable medical device before inserting a new supposedly sterile medical device. However, as seen above, antibiotic treatment (for example via intravenous line) very often turns out to be ineffective, only eliminating symptoms rather than the cause of the infection, such as the microbial biofilm.

The surgical procedure for replacing the implantable medical device is also not a solution as it leads to the implantation site being reopened and movement of the implantable medical device where the biofilm developed, with the significant risk of spreading it more (fracture, fragmentation of the biofilm and release of bacteria). In such a scenario, the bacteria protected by the biofilm may spread in the body, which may complicate the clinical situation rather than resolving it. Practically, it is not possible to remove an implant immediately after its placing when an infection related to the presence of biofilm occurs, particularly when the implant contributes to bone stability or performs a vital function in the body. Note that it is known that secondary implantations of other replacement medical devices carry the risk of infecting the new implanted devices, this being due to the dispersal of the biofilm after the removal of the initial implant.

Furthermore, the treatment of infections developed at the implantation sites of implantable medical devices is entirely different from that in place to fight against other infections related to the presence of biofilms in mammalian bodies, particularly in the human body. For example, a pulmonary infection which would be due to the presence of biofilms in the lung alveoli will not be treated in the same way as an infection resulting from the placing of an implantable medical device such as, for example, a pacemaker or a knee prosthesis. In that regard, although compositions intended for pre-implantation treatment exist, their application is not necessarily compatible with post-implantation treatment as the desired effect and the constraints encountered are different.

This results from the fact that the microorganisms colonising and developing on the implanted medical devices are of an entirely different nature as they develop in optimal temperature conditions (internal body temperature in the order of 37 to 38° C.) and in the presence of essential nutrients such as the sugars and proteins present in bodily fluids. In fact, the biofilms developing on and near the implanted medical devices have quite specific ratios between polymers and between bacterial colonies, which implies that these biofilms are characterised by a particular morphology and a specific composition giving them increased resistance to common removal treatments, for example using microbicidal molecules (antibiotics and/or biocides). Furthermore, each type of implant has a tendency to be infected by certain types of microorganisms, which is in large part due to the environment in which the implant can be found, as well as the surface of the implant itself. For example, in urinary catheters more than 50% of infections are caused by *E. coli, K. pneumoniae* and *E. faecalis*. In blood catheters, the majority are rather due to *Staphylococcus*-type bacteria.

There thus exists a real need to provide a composition for the removal of biofilms which can allow these problems to be solved, since the current solutions of pre-implantation treatments, heavy antibiotic treatment and replacement of the implantable medical devices by means of post-implantation surgery unfortunately do not allow the development of post-implantation infections at an implantation site related to the presence of biofilms in mammalian bodies, in particular in the human body, to be avoided and do not offer an effective curative solution to these post-implantation infections of mammalian bodies, in particular of the human body.

To solve this problem, a composition as indicated at the beginning is provided according to the invention, comprising at least one enzyme and at least one microbicidal molecule as combination products, for simultaneous use, separated use or use staggered over time, for use in preventative and/or curative treatment of infections at an implantation site, said infections being post-implantation infections of mammalian bodies, in particular post-implantation infections of the human body.

The term "post-implantation infections of mammalian bodies, in particular post-implantation infections of the human body" refers to, according to the present invention, infections which develop at and/or around an implantation site in mammalian bodies, in particular in the human body (in-vivo, in-situ, in place) following the placing of an implantable medical device (implant, prosthesis, gastric/urinary tube, drains, catheters, stents, etc.). These infections develop at and/or around an implantation site both on the implanted medical device or around it, for example in the tissues, bones and cartilage and/or the internal mucosa of the body. More particularly, according to the present invention, post-implantation infections of mammalian bodies, in particular of the human body, are infections caused by the development, after implantation and at an implantation site, of microorganisms in the form of biofilms following the implantation of a medical device provided to stay in the body for several hours, or several days, weeks, months or years, this not corresponding to a sample in which the medical device only passes a brief period of time in the body. More specifically, according to the present invention, post-implantation infections of mammalian bodies, in particular in the human body, are infections caused by a stay of at least 12 hours, more particularly of at least 24 hours of the implanted medical device in the body.

The term "microbicidal molecule" refers to, according to the present invention, a natural or synthetic molecule whose properties allow it to destroy (kill) microorganisms or to prevent the growth of microorganisms. According to the present invention, the term "microbicidal molecule" thus includes, though not exclusively, antibiotic and/or biocidal molecules.

It must be explained that, according to the present invention, it is a post-implantation type infection which is treated in a preventative or curative way at the site of implantation, in particular following the placing of an implantable medical device. It is not, as is the case in the compositions described in documents US2009/0130082 and WO2009/121183 for example, a pre-procedural treatment or a preparation of implantable medical devices, but rather a treatment applied after implantation (post-implantation) and at the implantation site.

In the scope of the present invention, it has been shown that use of such a composition allows post-implantation infections related to the presence of biofilms to be effectively treated, at and/or around the implantation site in mammalian bodies, in particular in the human body, without irreversibly damaging the tissues or internal mucosa of the body (deterioration, toxicity) in a way which does not aggravate the clinical situation of the patient (human or animal). Furthermore, it has been shown that the composition according to the invention allows the biofilm to be broken down by the action of at least one enzyme and to kill the majority of the bacterial colonies initially present in the biofilm at the implantation site. The simultaneous action, separated action or action staggered over time of at least one microbicidal molecule and at least one enzyme according to the invention is crucial as release of the microorganisms may allow them to spread through the body with all the risks which may come with delocalisation of the infection towards other more sensitive areas of mammalian bodies, in particular of the human body.

Unexpectedly, it has been shown that use of a composition according to the invention (at least one enzyme and at least one microbicidal molecule), formed solely of pharmaceutically acceptable components which are injectable or compatible with mammalian bodies, in particular with the human body, but able to comprise, though not necessary, other components, allows post-implantation infections at and/or around the implantation site to be treated by effectively and quickly breaking down the biofilms, however highly resistant, and particularly developing at and around and/or on the surfaces of the implanted medical devices.

Such a breakdown of these biofilms, however entirely specific, allows the microbicidal molecules (antibiotics and/or biocides) to effectively act on the microorganisms (bacteria and/or yeasts and/or archaea and/or viruses and/or prions and/or moulds) responsible for these infections. It was certainly not expected that a composition, particularly used for treating pulmonary infections or cleaning medical tools, could be used equally effectively to fight, at and/or around an implantation site, against post-implantation infections involving very resistant and very specific biofilms whose morphology and components (ratio of polymers, ratio of different bacteria colonies) are quite atypical through their association with implanted medical devices in an environment which is suitable for the development of biofilms.

Contrary to treatment by heavy antibiotics and surgical procedures aiming to replace an infected implanted medical device which is responsible for an infection, treatment, at and/or around an implantation site, of the post-implantation infections of mammalian bodies, in particular of the human body, related to the presence of biofilms, by use of a composition according to the invention has been shown to be highly effective. In that regard, use of a composition according to the invention systematically ensures treatment of the infection related to the presence of biofilm around the implantation site because it has been shown that at least one enzyme present in the composition according to the invention is capable of rapidly and versatilely breaking down numerous biofilms, however specific, thereby ensuring that the microbicidal molecules (antibiotics and/or biocides) reach the bacteria lacking any protective matrix.

In the scope of the present invention, surprisingly, use of a composition according to the invention has been identified as being capable of effectively treating, at and/or around the implantation site, infections related to the presence of particular biofilms formed by different associations of bacterial colonies and having very specific structural and morphological characteristics by their association with implanted medical devices. In particular, it has been observed that a composition according to the invention ensures, at and/or around the implantation site, an in-depth breakdown through the thickness of the biofilm even if the latter develops in optimal conditions and is consequently resistant to treatments which aim to eliminate it.

Treatment based on use of a composition according to the invention has also been identified as allowing, in a surprising way, an effective and quick treatment of post-implantation infections of mammalian bodies, in particular the human body, related to the presence of biofilms, to be carried out, i.e. an in-situ treatment at the place where the infection developed (at the implantation site), without involving any surgical procedure and without damaging the tissues and/or internal mucosa in the body in an irreversible manner (deterioration, breakdown, toxicity, etc.). For example, in the event of a urinary catheter whose implantation leads to an infection (urinary infection) related to the presence of biofilm, it is envisaged that the composition according to the invention could be injected into the urinary catheter so that the latter is flooded to simultaneously eliminate the biofilm forming the source of the infection and treat the infection. In the case of a prosthesis, for example a knee prosthesis, an in-situ treatment of the infection, which would be caused by the development of biofilm on and around the prosthesis, could be carried out by simple infiltration or injection (intra-articular injection, for example) of the composition according to the invention at the knee.

The composition used according to the invention is thus shown to be simultaneously versatile and effective in enabling rapid treatment, at the implantation site, of post-implantation infections related to the presence of quite particular biofilms which, to this day, heavy antibiotic treatment or a surgical procedure aiming to provide solutions are revealing that they are only partially, if at all, effective, as indicated above. Furthermore, use of a composition according to the invention has been identified as allowing rapid integration of the implanted medical device to be carried out, particularly by allowing faster healing at the implantation site, this thanks to the absence of biofilm, ensured by the composition according to the invention. Indeed, in a surprising and advantageous manner, it has been determined that a composition according to the invention is not cytotoxic even though it is highly effective for destroying (killing) the bacteria initially protected by the biofilms and for eliminating the biofilms and microorganisms from the treated surfaces.

As will become apparent from the examples given below, different combinations of at least one enzyme with at least one microbicidal molecule (antibiotic) lead to the effective treatment of various infections related to the presence of biofilms formed by various bacterial species and strains. The compositions according to the invention are thus versatile and lead to treatment of a large range of post-implantation infections.

Advantageously, said at least one enzyme of the composition according to the invention for use in the treatment, at an implantation site, of post-implantation infections of mammalian bodies, in particular of the human body, is chosen from the group composed of deoxyribonucleases (DNases), lipases, proteases and polysaccharide hydrolases including Dispersin B and cellulase.

Preferably, said at least one enzyme of the composition according to the invention for use in the treatment, at an implantation site, of post-implantation infections of mammalian bodies, in particular of the human body, is supplied in an administrable volume of between 100 and 100,000 µL.

Advantageously, said at least one enzyme of the composition according to the invention for use in the treatment, at an implantation site, of post-implantation infections of mammalian bodies, in particular of the human body, is supplied in a concentration between 0.01 and 1000 mg/L. In the event where said at least one enzyme of the composition according to the invention is administered in the form of a powder (lyophilisate) or a tablet, for example, said enzyme is supplied in a quantity by dry weight of between 0.01 and 50,000 mg/kg with respect to the total dry weight of said powder (lyophilisate) or to the total dry weight of said tablet.

Preferentially, said at least one microbicidal molecule of the composition according to the invention for use in the treatment, at an implantation site, of post-implantation infections of mammalian bodies, in particular of the human body, is supplied in an administrable volume of between 100 and 100,000 µL.

Preferably, said at least one microbicidal molecule of the composition according to the invention for use in the treatment, at an implantation site, of post-implantation infections of mammalian bodies, in particular of the human body, is supplied in a concentration of between 0.01 and 1000 mg/L. In the event where said microbicidal molecule of the composition according to the invention is administered in the form of a powder (lyophilisate) or a tablet, for example, said microbicidal molecule is supplied in a quantity by dry weight of between 0.01 and 10,000 mg/kg with respect to the total dry weight of said powder (lyophilisate) or to the total dry weight of said tablet.

Preferably, said at least one microbicidal molecule of the composition according to the invention for use in the treatment, at an implantation site, of post-implantation infections of mammalian bodies, in particular of the human body, is chosen from the group composed of fluoroquinolones, glycopeptides, lipoglycopeptides, fusidic acid, penicillins, cephalosporins, carbapenems, monobactams, polymyxins, beta-lactams, macrolides, lincosamides, oxazolidinones, amphenicols, tetracyclines, aminoglycosides, rifamycins, nitrofurans, sulphonamides, nitroimidazoles, antifungals (echinocandins, fluorocytosines, azoles, griseofulvins), lytic enzymes (for example endolysins or lysozyme), N-acetyl-cysteine, quaternary ammonium, biguanides, amines, halogenated derivatives (particularly of chlorhexidine), antimicrobial peptides, silver (Ag) derivatives, $H_2O_2$ derivatives, peroxy acids, phenolic derivatives, aldehydes, alcohols and mixtures thereof.

Advantageously, the composition according to the invention for use in the treatment, at an implantation site, of post-implantation infections of mammalian bodies, in particular of the human body, is supplied in the form of a sterile aqueous solution which may be injected or not, which may be diluted or not in water for injectable preparation or in the form of a soluble powder, preferably in the form of a lyophilisate.

Preferably, the composition according to the invention for use in the treatment, at an implantation site, of post-implantation infections of mammalian bodies, in particular of the human body, comprises a pharmaceutically acceptable carrier and/or excipient such as, for example, a stabilising agent provided to ensure the stability of the composition in storage so the composition does not deteriorate before use.

Advantageously, the composition according to the invention for use in the treatment, at an implantation site, of post-implantation infections of mammalian bodies, in particular in the human body, is packaged in a sterile container, for example in a sterile flask provided with a cap through which water for injectable preparation may be injected so the composition according to the invention can be formed.

Preferentially, said post-implantation infections of mammalian bodies, in particular of the human body, treated, at an implantation site, with the composition according to the invention are post-implantation infections of the following bacteria: *Staphylococcus aureus, Staphylococcus epidermis, Escherichia coli, Escherichia faecalis, Klebsiella pneumoniae* and *Pseudomonas aeruginosa*. For example, the post-implantation infections in the scope of the present invention may be urinary infections (catheters), dental peri-implantitis (endosseous implants, zygomatic implants, orthodontic implants, retention plates), endocarditis (heart valves, stents), surgical wounds (catheter point of entry), otitis (drains), pulmonary infections, of the larynx and throat (artificial breathing tubes), sinus infections (drains), renal infections (stents, catheters), gastric infections (tubes), hepatic infections (stents), pancreatic infections (stents), enteric infections (tubes) and colon infections (tubes), bone and cartilage infections (plates, screws and prostheses), infections of the brain stem (stents) and circulatory infections (catheters).

According to the present invention, the infections may also be caused by yeasts (for example by *Candida albicans*), by organisms causing mycosis (for example by *Aspergillus*) and by other bacteria (for example by *Proteus mirabilis, Enterobacter, Citrobacter* or *Acinetobacter*).

Preferably, according to the invention, said post-implantation infections of mammalian bodies, particularly of the human body, are infections localised at an implantation site of an implantable medical device, for example a tube, catheter or prosthesis.

Advantageously, the composition according to the invention for use in the treatment, at an implantation site, of post-implantation infections of mammalian bodies, in particular in the human body, is provided to kill at least 1 Log 10, preferably at least 2 Log 10, preferentially at least 5 Log 10 of the microorganisms responsible for post-implantation infections of mammalian bodies, in particular of the human body.

The present invention also relates to a use of a composition comprising at least one enzyme and at least one microbicidal molecule as combination products, for simultaneous use, separated use or use staggered over time, for the treatment, at an implantation site, of post-implantation infections of mammalian bodies, in particular of the human body.

Preferably, the use of a composition according to the invention comprising at least one enzyme and at least one microbicidal molecule is administered by injection, by infiltration, by irrigation, by ingestion or by percutaneous application. In the scope of the present invention, said administration may be carried out by means of a gel, ointment, cream or via a patch. Note that the present invention provides simultaneous administration, separated administration or administration staggered over time of the combination products that are said at least one enzyme and said at least one microbicidal molecule, this certainly not imposing that the administration modes (methods) of these combination products are identical.

The present invention also relates to a method for treating, at an implantation site, post-implantation infections of mammalian bodies, in particular of the human body, with a composition comprising at least one enzyme and at least one microbicidal molecule as combination products, for simultaneous use, separated use or use staggered over time, said method comprising the following steps:

administration, at an implantation site of an implantable medical device, of a composition comprising at least one enzyme and least one microbicidal molecule, breakdown, by action of said at least one enzyme of said administered composition, of a biofilm present at said implantation site of said implantable medical device, and destruction of bacteria and/or inhibition of the growth of bacteria released from said biofilm, by action of said at least one microbicidal molecule of said administered composition.

Advantageously, according to the method for treating, at an implantation site, post-implantation infections of mammalian bodies, in particular of the human body, said administration is carried out by injection, by infiltration, by irrigation, by ingestion or by percutaneous application. In the scope of the present invention, said administration may be carried out by means of a gel, ointment, cream, liquid solution or via a patch.

Other features, details and advantages of the invention will become clear in the examples and appended figures.

FIG. 1 is a graph which illustrates the viability of the bacteria from an isolate of *S. aureus* (isolated from an implanted pacemaker) having developed a biofilm, following contact either with a composition according to the invention (ciprofloxacin as an antibiotic molecule at 3.2 mg/L+0.025% DNase I, 0.01% Dispersin B and 0.05% cellulase), or with a composition solely comprising ciprofloxacin as an antibiotic molecule at 3.2 mg/L.

FIG. 2 is a graph which illustrates the viability of the bacteria from an isolate of *E. coli* (isolated from an implanted urinary catheter) having developed a biofilm, following contact either with a composition according to the invention (ciprofloxacin as an antibiotic molecule at 3.2 mg/L+0.025% DNase I, 0.01% Dispersin B and 0.05% cellulase), or with a composition solely comprising ciprofloxacin as an antibiotic molecule at 3.2 mg/L.

Figure 3:
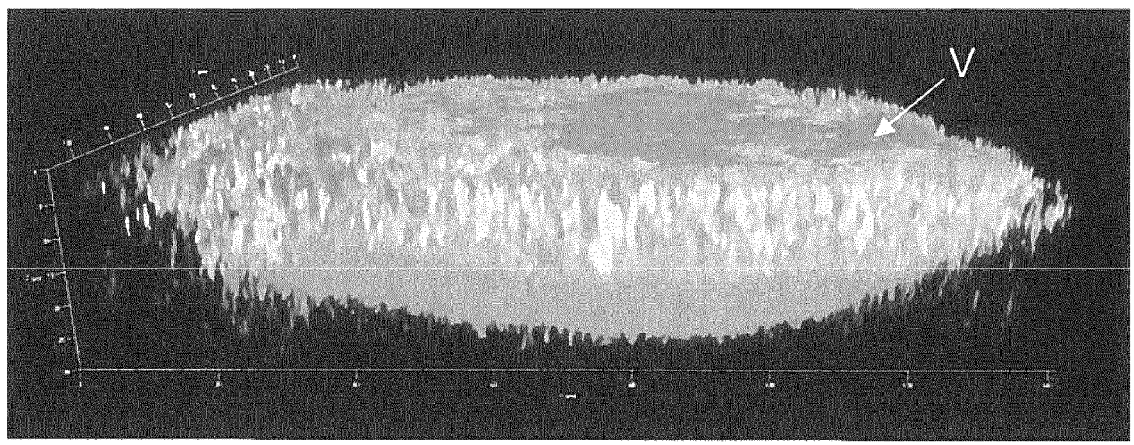
FIG. 3 is a confocal microscopic image of an isolate of *S. aureus* (isolated from an implanted pacemaker) having developed a biofilm over 24 h.

FIGS. 7*a* to 7*d* are graphs which illustrate the viability (% of viability with respect to the control) of the bacteria of an isolate of *P. aeruginosa* PA20 (isolated from an implanted arterial catheter) having developed a biofilm, following contact with different antibiotics of Cmin concentration in combination with different enzymes or a cocktail of enzymes.

FIGS. 8a to 8d are graphs which illustrate the viability (% of viability with respect to the control) of the bacteria of an isolate of *P. aeruginosa* PA500 (isolated from an implanted arterial catheter) having developed a biofilm, following contact with different antibiotics of Cmin concentration in combination with different enzymes or a cocktail of enzymes.

FIG. 9 is a graph which illustrates the viability (% of viability with respect to the control) of the bacteria of an isolate of *S. aureus* Sa2003/1083 (isolated from a knee prosthesis) having developed a biofilm, following contact with different antibiotics of Cmin concentration in combination with different enzymes or a cocktail of enzymes.

FIGS. 10a to 10c are graphs which illustrate the viability (% of viability with respect to the control) of the bacteria of an isolate of *K. pneumoniae* Kp826 (isolated from a central venous catheter) having developed a biofilm, following contact with different antibiotics of Cmin concentration in combination with different enzymes or a cocktail of enzymes.

FIGS. 11a to 11f are graphs which illustrate the cytotoxicity of compositions according to the invention on human cell lines.

EXAMPLES

Example 1

Effectiveness and Cytotoxicity of a First Composition According to the Invention Used in the Treatment of Post-Implantation Infections A. Effectiveness In order to test the effectiveness of a composition according to the invention comprising at least one enzyme and at least one biocidal and/or antibiotic molecule (microbicidal molecule) to treat post-implantation infections of mammalian bodies, in particular of the human body, several experiments were conducted from isolates taken from medical devices infected by biofilms in the human body following their implantation. These isolates are listed in Table 1 below.

Three different experiments, carried out according to three biofilm models, were conducted: (1) static model of in-vitro biofilm, (2) dynamic model of in-vitro biofilm and (3) dynamic model of biofilm in a bioreactor.

Furthermore, confocal microscopic images were taken for an isolate in order to visualise the dispersal of the bacteria and the effectiveness of a composition according to the invention in terms of bacteria survival.

To carry out these experiments, different compositions according to the invention were prepared under agitation (120 RPM) by dilution of at least one antibiotic and/or biocidal molecule in an aqueous solution (water buffered with 20 mM tris(hydroxymethyl)aminomethane and with a pH of 7.5) comprising at least one enzyme. For the tests presented below, ciprofloxacin was used as the antibiotic molecule.

In order to judge the effectiveness of a post-implantation treatment carried out with a composition according to the invention, the viability of the bacteria was measured by following the development of the colour of the resazurin (7-Hydroxy-3H-phenoxazin-3-on 10-oxide), this colour changing according to the redox potential which depends on microbial activity. The measurement was conventionally carried out by absorption photometry (measurement at 590 nm with the Spectramax M4 equipment). Based on the values measured for different concentrations of the antibiotic and/or biocidal molecule in the presence of an enzymatic composition fixed in the composition according to the invention, the dose-response curves, and more particularly the $EC_{50}$, that is the necessary concentration of the antibiotic and/or biocidal molecules for ensuring a 50% reduction of the viability of the bacteria, which corresponds to a 50% reduction of the size of the signal measured by absorption photometry, were determined.

| Isolate | Strain | Bacteria | Origin |
|---|---|---|---|
| 1 | 80124430375 | *S. aureus* MRSA | pacemaker |
| 2 | 80224422456 | *S. aureus* MRSA | knee prosthesis |
| 3 | 80124474762 | *S. aureus* MRSA | knee screw |
| 4 | 80224420266 | *S. epidermis* | central venous catheter (CVC) |
| 5 | 6081 | *E. coli* | urinary catheter |
| 6 | 5701 | *E. coli* | orthopaedic implant |
| 7 | 9794 | *E. faecalis* | urinary catheter |
| 8 | 9781 | *E. faecalis* | urinary catheter |
| 9 | 9555 | *E. faecalis* | urinary catheter |
| 10 | DIV5508 | *P. aeruginosa* | central venous catheter (CVC) |
| 11 | 04/190 | *P. aeruginosa* | urinary catheter |

1. Static Model of In-Vitro Biofilm

From each of the isolates given in table 1, biofilms (n=4) were developed over 24 hours at a temperature of 37° C. in the wells of a 96-well plate containing 200 μL of a TSB culture medium (Tryptic Soy Broth VWR) supplemented with 1% glucose and 2% sodium chloride.

Then, over a second 24-hour period, the biofilms developed in the wells were subjected to growing concentrations (from 0.15 to 40 mg/L) of ciprofloxacin as an antibiotic in an aqueous solution comprising 0.025% DNase I (VWR), 0.01% Dispersin B (Symbiose Biomaterials) and 0.05% cellulase (Carezyme® of Novozyme).

It should be noted here that the enzyme percentages are in wt % which express the quantities by the weight of each commercial enzyme with respect to the total weight of the composition. This applies to the entirety of this document.

Before proceeding with the measurement of the viability of the bacterial cells with resazurin, the plates containing the developed biofilms were washed with a PBS buffer (pH=7.4) then incubated with resazurin (0.01 mg/L) for 1 hour in the dark.

The results obtained are listed in Table 2 below which presents, based on the established dose-response curves, the concentrations (mg/L) necessary in the antibiotic molecule in order to reduce the viability of the studied bacteria having developed a biofilm by 50%, also known as $EC_{50}$ (which corresponds to a 50% reduction of the size of the signal measured by absorption photometry).

The increase in activity of the antibiotic molecule, or the decrease of its $EC_{50}$, when it is linked to 0.025% DNase I, 0.01% Dispersin B and 0.05% cellulase, is also given in Table 2 (ratio of $EC_{50}$:solution B/solution A).

As can be seen, for each of the isolates tested, a composition according to the invention allowed the activity of the antibiotic molecule to be systematically increased in a significant manner, also known as reducing the $EC_{50}$ in a significant manner. These results indicate, in comparison with a composition only containing the antibiotic molecule, that the bacteria were reached and killed by the molecule in a much more effective manner. This is explained by the presence of enzymes which truly break the biofilm down in such a way that the bacteria are released and then come into direct contact with the antibiotic molecule.

TABLE 2

| Isolate | Concentration of the antibiotic molecule in a solution comprising the antibiotic alone (solution A) to reduce the viability of the bacteria by 50% ($EC_{50}$) | Concentration of the antibiotic molecule in a solution comprising the antibiotic in association with 0.025% DNase I, 0.01% Dispersin B and 0.05% cellulase (solution B) to reduce the viability of the bacteria by 50% ($EC_{50}$) | Increase in activity of the antibiotic molecule |
|---|---|---|---|
| 1 | >40[a] | 1.5 | >26.6 |
| 2 | 0.8 | 0.1 | 8 |
| 3 | 1.2 | 0.2 | 6 |
| 4 | 1.77 | 0.08 | 22.1 |
| 5 | 2.7 | 0.11 | 24.5 |
| 6 | >40 | 0.23 | >173.9 |
| 7 | >40 | 0.25 | >160 |
| 8 | >40 | 1.4 | >28.5 |
| 9 | >40 | 2.5 | >16 |
| 10 | >40 | 1.26 | >31 |
| 11 | >40 | 0.05 | >792 |

[a] >40 means that the 50% reduction of the microbial population for a concentration of 40 mg/L in the antibiotic did not occur. The $EC_{50}$ is thus greater than 40 mg/L.

2. Dynamic Model of In-Vitro Biofilm

20 μL of liquid culture from isolates 1 and 5 (n=4) was inoculated in the wells of a 96-well plate containing 180 μL of a TSB culture medium (Tryptic Soy Broth VWR) supplemented with 1% glucose and 2% sodium chloride then a PEG platform was immersed so the biofilms developed on the PEG protrusions for 48 hours at a temperature of 37° C. under constant agitation at 120 RPM.

Then, over a second 24-hour period, the biofilms developed in the wells on the protrusions were subjected, still under constant agitation at 120 RPM, to growing concentrations (from 0.15 to 40 mg/L) of ciprofloxacin as an antibiotic in an aqueous solution comprising 0.025% DNase I (VWR), 0.01% Dispersin B (Symbiose Biomaterials) and 0.05% cellulase (Carezyme® of Novozyme).

Before proceeding with the measurement of the viability of the bacterial cells with resazurin, the PEG plates with the protrusions containing the developed biofilms were incubated with resazurin for 2 hours in the dark.

The results obtained are listed in Table 3 below which presents, based on the established dose-response curves, the concentrations (mg/L) necessary of the antibiotic molecule in order to reduce the viability of the studied bacteria having developed a biofilm by 50% (which corresponds to a 50% reduction of the size of the signal measured by absorption photometry). The increase in activity of the antibiotic molecule, or the decrease of its $EC_{50}$, when it is linked to 0.025% DNase I, 0.01% Dispersin B and 0.05% cellulase, is also given in Table 2 (ratio of $EC_{50}$:solution B/solution A).

As can be seen, for isolates 1 (S. aureus isolated from a pacemaker on which a biofilm developed in the human body after implantation) and 5 (E. coli isolated from a urinary catheter on which a biofilm developed in the human body after implantation), a composition according to the invention allows the activity of the antibiotic molecule to be systematically increased, also reducing the $EC_{50}$, in a significant manner.

| Isolate | Concentration of the antibiotic molecule in a solution comprising the antibiotic alone (solution A) to reduce the viability of the bacteria by 50% ($EC_{50}$) | Concentration of the antibiotic molecule in a solution comprising the antibiotic in association with 0.025% DNase I, 0.01% Dispersin B and 0.05% cellulase (solution B) to reduce the viability of the bacteria by 50% ($EC_{50}$) | Increase in activity of the antibiotic molecule |
|---|---|---|---|
| 1 | 0.7 | 0.001 | 700 |
| 5 | 3.18 | 0.004 | 795 |

These results indicate, in comparison with a composition only containing the antibiotic molecule, that the bacteria were reached and killed by the molecule in a much more effective manner. This is explained by the presence of enzymes which truly break the biofilm down in such a way that the bacteria are released and then come into direct contact with the antibiotic molecule.

3. Dynamic Model of Biofilm in a Bioreactor

Isolates 1 and 5 (n=3) were inoculated on polycarbonate coupons then placed in a CDC bioreactor (BioSurfaces Technologies) containing 300 ml of a TSB culture medium (Tryptic Soy Broth VWR) supplemented with 1% glucose and 2% sodium chloride in order to develop biofilms for 20 hours at a temperature of 37° C. under constant agitation at 120 RPM. The development was more particularly carried out in two successive phases, namely (1) a first incubation phase of 6 hours at a bacterial concentration of $10^5$ bacteria/ml and (2) a second phase of 14 hours during which continuous circulation at 10 ml/minute of the culture medium was carried out in the bioreactor through use of a peristaltic pump (Masterflex). Following this development of biofilms carried out in two phases, the latter were subjected, in the bioreactor, to a concentration of 3.2 mg/L of ciprofloxacin as an antibiotic in an aqueous solution comprising 0.025% DNase I (VWR), 0.01% Dispersin B (Symbiose Biomaterials) and 0.05% cellulase (Carezyme® of Novozyme).

The coupons were then aseptically removed after 0, 4, 8, 12, 18 and 24 hours and rinsed twice in a PBS buffer before sonication of the formed biofilms. Successive dilutions in a PBS buffer (pH=7.4) were then carried out from the samples thus obtained before plating on a TSA culture medium (VWR) for counting the bacterial colonies ($Log_{10}$ CFU/ml) following incubation of the culture media for 18 hours at a temperature of 37° C. and a relative humidity of 60%.

The results obtained are presented in FIGS. 1 and 2 from which it is again made clear that, for each of the isolates tested, a composition according to the invention allows the activity of the antibiotic molecule to be systematically increased in a significant manner. In fact, regarding isolate 1 (S. aureus isolated from a pacemaker on which a biofilm developed in the human body after implantation), a logarithmic reduction in the order of 5 of the number of live bacteria was observed in comparison with a logarithmic reduction in the order of 0.5 when the antibiotic molecule was used alone (see FIG. 1). The same observation was conducted for isolate 5 (E. coli isolated from an urinary catheter on which a biofilm developed in the human body after implantation): logarithmic reduction in the order of 5 of the number of live bacteria during treatment with a composition according to the invention and in the order of 0.5 for a composition containing only the antibiotic (see FIG. 2).

These results indicate, in comparison with a composition only containing the antibiotic molecule, that the bacteria were reached and killed by the molecule in a much more effective manner. This is explained by the presence of enzymes which truly break the biofilm down in such a way that the bacteria are released and then come into direct contact with the antibiotic molecule.

4. Confocal Microscopic Images

Figure 4:
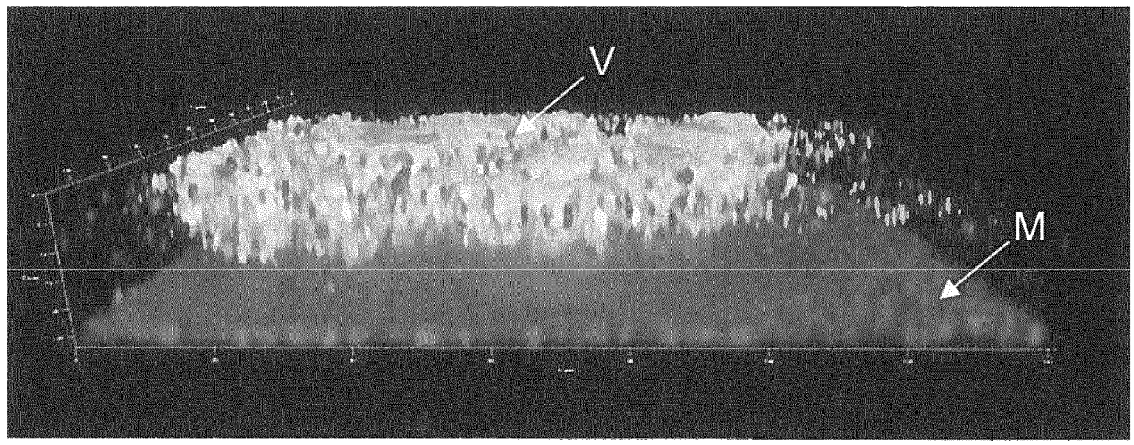
FIG. 4 is a confocal microscopic image of an isolate of *S. aureus* (isolated from an implanted pacemaker) having developed a biofilm over 24 h and then treated with a composition solely comprising ciprofloxacin as an antibiotic molecule at 1 mg/L over 24 h.
Figure 5:
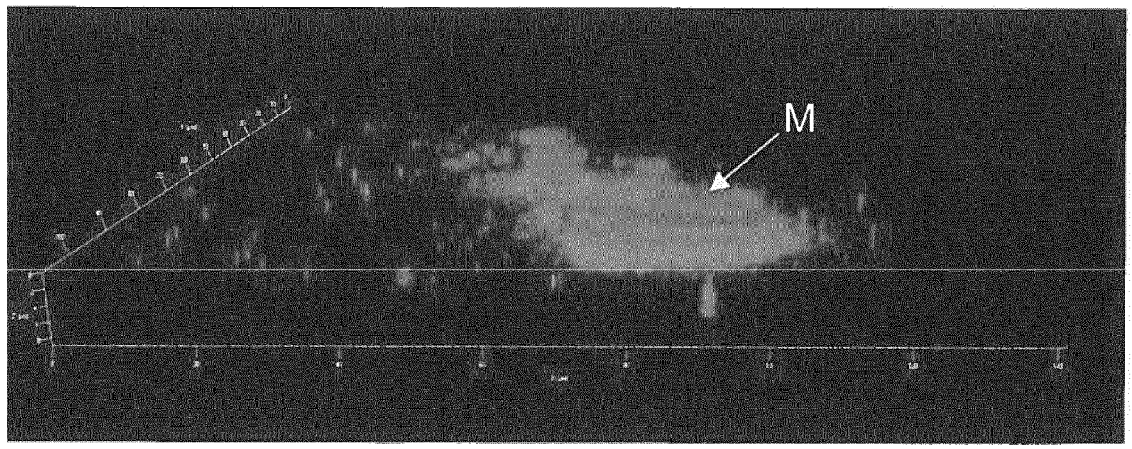
FIG. 5 is a confocal microscopic image of an isolate of *S. aureus* (isolated from an implanted pacemaker) having developed a biofilm over 24 h and then treated with a composition according to the invention (ciprofloxacin at 1 mg/L+0.025% DNase I+0.01% Dispersin B+0.05% cellulase) over 24 h.

For isolate 1 (S. aureus isolated from a pacemaker on which a biofilm developed in the human body after implantation), confocal images were taken and correspond to FIGS. 3 to 5. FIG. 3 corresponds to an image of the biofilm developed by isolate 1 over 24 h; FIG. 4 corresponds to an image of the biofilm developed by isolate 1 over 24 h after treatment (incubation) with a composition containing only the antibiotic molecule (ciprofloxacin at 1 mg/L) for 24 h; FIG. 5 corresponds to an image of the biofilm developed over 24 h by isolate 1 after treatment (incubation) with a composition according to the invention (ciprofloxacin at 1 mg/L+0.025% DNase I+0.01% Dispersin B+0.05% cellulase) for 24 h.

Before obtaining the different images, staining was carried out with the LIVE/DEAD kit (Invitrogen) for 30 minutes before rinsing with a PBS buffer.

From these confocal images it appears that, as for the tests with the biofilm models above, a composition according to the invention is much more effective than a composition not containing the antibiotic molecule. In fact, FIG. 5 (treatment with a composition according to the invention) shows that all the bacteria have been killed (destroyed) (M) whereas FIG. 4 (treatment with the antibiotic molecule alone) shows, on the contrary, that numerous bacteria are still alive (V). As before, this is explained by the presence of enzymes which will truly break the biofilm down in such a way that the bacteria are released and then come into direct contact with the antibiotic molecule.

B. Cytotoxicity

In order to judge the cytotoxicity of a composition according to the invention used in the treatment of post-implantation infections of mammalian bodies, in particular of the human body, three human cell lines, THP-1, U937 and HL-60, were used. For each line, cells ($10^4$ cells/ml) were incubated for 4 h in the wells of a 96-well plate in the presence of an enzymatic cocktail according to the invention (0.025% DNase I+0.01% Dispersin B+0.05% cellulase) or in the presence of each of these enzymes at the same concentration as they are in the enzymatic cocktail (DNase I–DNase or Dispersin B–DispB or cellulase–Carezyme).

The cytotoxicity was evaluated based on the amount of lactate dehydrogenase (LDH) present in the supernatant by using the PLUS detection kit (Roche, Basel, Switzerland). The level of LDH naturally salted-out by the non-treated cells of each line was measured (negative control) as well as the maximum level of LDH released by the same cells (positive control). The cytotoxicity was calculated according to the following formula: (value measured from the sample–value of the negative control)/(value of the positive control–value of the negative control)×100.

Figure 6:
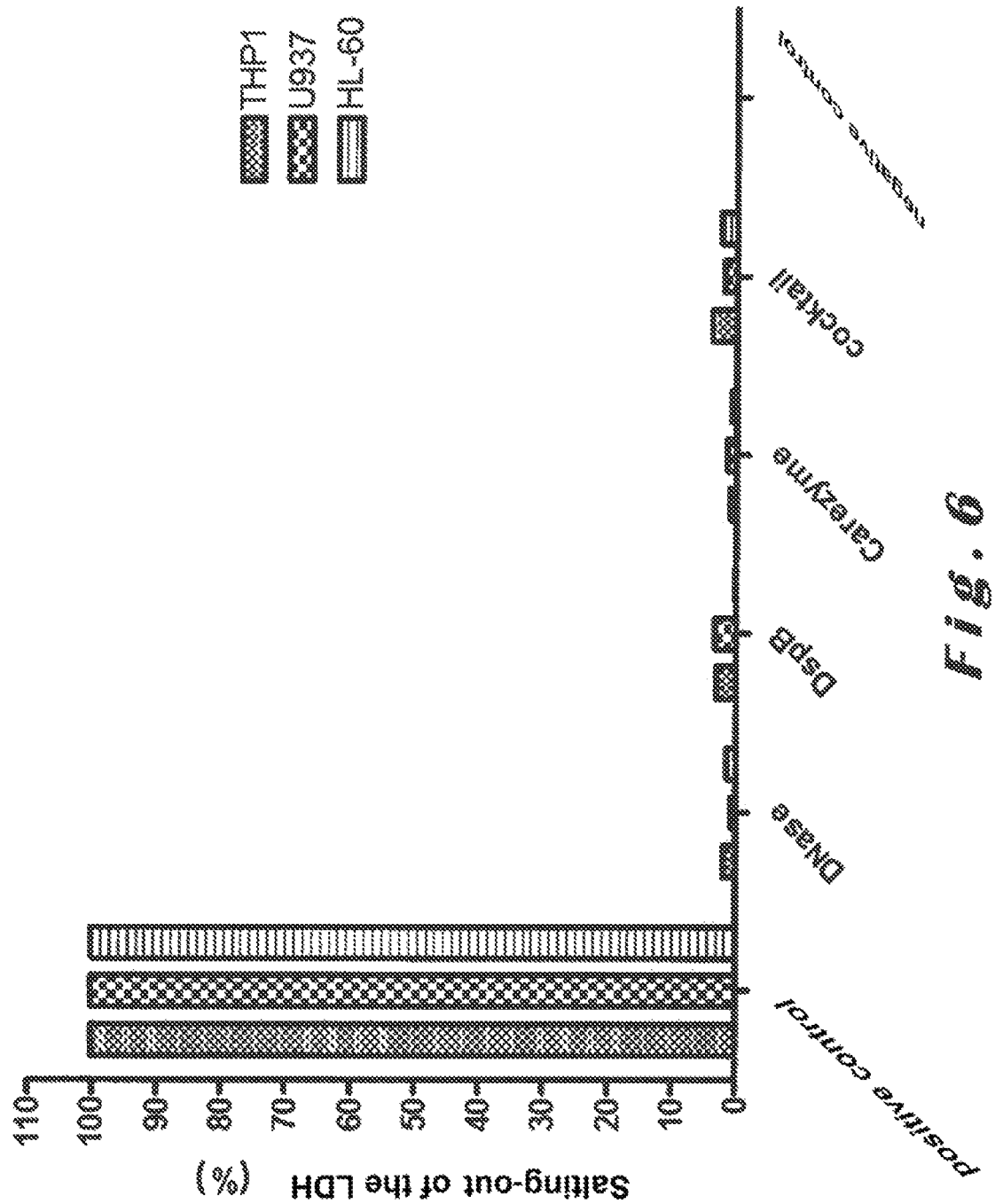
FIG. 6 is a graph which illustrates the cytotoxicity of DNase I, Dispersin B and cellulase alone or linked to human cell lines.

The results obtained are presented in FIG. 6 where it can be seen that the enzymatic cocktail, like each of the enzymes, according to the invention shows no toxicity for human cell lines.

Example 2

Effectiveness and Cytotoxicity of Different Compositions According to the Invention Used in the Treatment of Post-Implantation Infections Compositions other than that described in Example 1 were tested in terms of effectiveness and cytotoxicity in order to establish that different combinations of enzymes with different microbicidal molecules (antibiotics) are able to provide treatment for post-implantation infections. The object of the tests carried out in Example 2 is essentially to highlight that the present invention is not limited to a particular composition such as that of Example 1, but that a whole range of different combinations and thus different compositions according to the invention are effective in the treatment of post-implantation infections.

Different clinical strains were isolated from medical devices infected by biofilms in the human body following their implantation. These isolates, as well as their origins, are listed in Table 4 below.

TABLE 4

| Strain | Bacterial species | Origin |
| --- | --- | --- |
| PA20 | P. aeruginosa | arterial catheter |
| PA500 | P. aeruginosa | arterial catheter |
| Sa2003/1083 | S. aureus MRSA | knee prosthesis |
| Kp826 | K. pneumoniae | central venous catheter |

A. Effectiveness: Static Model of In-Vitro Biofilm a) Culturing and Formation of Biofilm from Isolates of P. aeruginosa (PA20 and PA500)

5 μL of a glycerol stock of PA20 or PA500 was added to 5 ml of LB-glucose culture medium (medium formed of a mixture of Luria Bertani (LB) and 1% glucose) and incubated for 24 h at 37° C. The bacterial suspension was then diluted with the LB-glucose medium in order to obtain an inoculum of $10^6$ bacteria/ml.

The biofilms were cultivated on 96-well plates following an addition of 200 μL of the inoculum in each well. The plates were then incubated at 37° C. for 48 h with a replenishment of the medium after 24 h.

The biofilms obtained were then treated for 24 h with different enzymes (Dispersin B, DNase, cellulase (carezyme), savinase (protease), lipolase (lipase), amylase (stainzyme) and mannanase) in combination with different antibiotics at maximum concentration (Cmax) or minimum concentration (Cmin), Cmax being the maximum serum concentration after administration of the antibiotic and Cmin the minimum serum concentration. These concentrations Cmin and Cmax are based on those recommended by EUCAST (The European Committee on Antimicrobial Susceptibility Testing).

The treatments of the biofilm with the use of different combinations of an antibiotic with one or several enzymes were carried out in accordance with the following concentrations of antibiotics and enzymes:

enzymes: 0.05%; DCC=0.025% DNase+0.01% Dispersin B (DspB)+0.05% cellulase (Ce)
amikacin: Cmin=5 mg/L (Cmax=24 mg/L)
tobramycin: Cmin=0.9 mg/L (Cmax=4 mg/L)
moxifloxacin: Cmin=0.3 mg/L (Cmax=3.6 mg/L)
meropenem: Cmin=0.1 mg/L (Cmax=20 mg/L)
ciprofloxacin: Cmin=0.6 mg/L (Cmax=3.2 mg/L)

Fluorescein diacetate (FDA) was used to measure the viable *P. aeruginosa* (PA20 or PA500) bacteria. The plates containing the biofilms were washed twice with an MOPS buffer then incubated in FDA (100 µg/ml) for 1 h in the dark. FDA is a non-fluorescent hydrolysable in a fluorescent yellow component (fluorescein) by non-specific intracellular esterases produced by the viable bacteria. The measurement was carried out by spectrophotometry (length of excitation wavelength at 494 nm and transmission at 518 nm) with a spectramax M4. The amount of fluorescein measured by fluorimetry is directly proportional to the number of viable bacteria in the medium. The results obtained are presented in FIGS. 7 and 8.

FIGS. 7*a* to 7*d* illustrate the viability (% of viability with respect to the control—non-treated) of the bacteria of an isolate of *P. aeruginosa* PA20 (isolated from an implanted arterial catheter) having developed a biofilm, following contact with (A) amikacin at Cmin concentration as an antibiotic in combination with savinase (Say) as the sole enzyme or with lipolase (Li) as the sole enzyme or with savinase (Say) and lipolase (Li) as enzymes or with Dispersin B (DspB), DNase and cellulase (Ce) as enzymes (DCC);

(B) tobramycin at Cmin concentration as an antibiotic in combination with savinase (Say) as the sole enzyme or with amylase (Am) as the sole enzyme or with savinase (Say) and amylase (Am) as enzymes or with Dispersin B (DspB), DNase and cellulase (Ce) as enzymes (DCC);

(C) moxifloxacin at Cmin concentration as an antibiotic in combination with savinase (Say) as the sole enzyme or with mannanase (Ma) as the sole enzyme or with savinase (Say) and mannanase (Ma) as enzymes or with Dispersin B (DspB), DNase and cellulase (Ce) as enzymes (DCC);

(D) meropenem at Cmin concentration as an antibiotic in combination with DNase as the sole enzyme or with mannanase (Ma) as the sole enzyme or with DNase and mannanase (Ma) as enzymes or with Dispersin B (DspB), DNase and cellulase (Ce) as enzymes (DCC).

FIGS. 8*a* to 8*d* illustrate the viability (% of viability with respect to the control—non-treated) of the bacteria of an isolate of *P. aeruginosa* PA500 (isolated from an implanted arterial catheter) having developed a biofilm, following contact with (A) ciprofloxacin at Cmin concentration as an antibiotic in combination with savinase (Say) as the sole enzyme or with lipolase (Li) as the sole enzyme or with savinase (Say) and lipolase (Li) as enzymes or with Dispersin B (DspB), DNase and cellulase (Ce) as enzymes (DCC);

(B) amikacin at Cmin concentration as an antibiotic in combination with DNase as the sole enzyme or with lipolase (Li) as the sole enzyme or with DNase and lipolase (Li) as enzymes or with Dispersin B (DspB), DNase and cellulase (Ce) as enzymes (DCC);

(C) tobramycin at Cmin concentration as an antibiotic in combination with DNase as the sole enzyme or with savinase (Say) as the sole enzyme or with DNase and savinase (Say) as enzymes or with Dispersin B (DspB), DNase and cellulase (Ce) as enzymes (DCC);

(D) moxifloxacin at Cmin concentration as an antibiotic in combination with DNase as the sole enzyme or with savinase (Say) as the sole enzyme or with DNase and savinase (Say) as enzymes or with Dispersin B (DspB), DNase and cellulase (Ce) as enzymes (DCC).

In the graphs of FIGS. 7*a* to 7*d* and 8*a* to 8*d* the results of a statistical test are shown (One-way ANOVA with multiple comparison Dunnett's test) carried out in order to determine if a significant difference can be observed between the Cmax of the antibiotic and the Cmin of the antibiotic associated with one or several enzymes. The characters *,  and * respectively mean $p<0.05$, $p<0.01$ and $p<0.001$.

From these graphs, it can be observed that all the combinations [antibiotic at Cmin+enzyme(s)] tested allow the viability of the bacteria of the *P. aeruginosa* species (both for the PA20 strain and the PA500 strain of *P. aeruginosa*) to be reduced in a significant manner (p value at least less than 0.05) in comparison to the sole antibiotic at a concentration of Cmax. Similarly, it can be noted that a significant difference was observed between all the combinations [antibiotic at Cmin+enzyme(s)] tested and the control (non-treated biofilm), which is not the case for a comparison between the effect of the antibiotic alone (at Cmin or Cmax) and the control (non-treated biofilm).

This shows the advantage of combining an antibiotic and at least one enzyme for the preventative and/or curative treatment of post-implantation infections at an infection site, said infections being post-implantation infections.

b) Culturing and Formation of Biofilm from Isolates of *S. aureus* (Sa2003/1083) and *K. pneumoniae* (Kp826)

5 µL of a glycerol stock of Sa2003/1083 or Kp826 was added to 5 ml of TGN medium (medium formed of a mixture of Tryptic Soy Broth, 1% glucose and 2% NaCl) and incubated for 24 h at 37° C. The bacterial suspension was then diluted with the TGN medium in order to obtain an inoculum of $10^6$ bacteria/ml.

The biofilms were cultivated on 96-well plates following an addition of 200 µL of the inoculum in each well. The plates were then incubated at 37° C. for 24 h.

The biofilms obtained were then treated for 24 h with different enzymes in combination with different antibiotics at Cmax or Cmin.

The treatments of the biofilm with the use of different combinations of an antibiotic with one or several enzymes were carried out in accordance with the following concentrations of antibiotics and enzymes:

enzymes: 0.05%; DCC=0.025% DNase+0.01% Dispersin B (DspB)+0.05% cellulase (Ce)
amikacin: Cmin=5 mg/L (Cmax=24 mg/L)
tobramycin: Cmin=0.9 mg/L (Cmax=4 mg/L)
moxifloxacin: Cmin=0.3 mg/L (Cmax=3.6 mg/L)
meropenem: Cmin=0.1 mg/L (Cmax=20 mg/L)
ciprofloxacin: Cmin=0.6 mg/L (Cmax=3.2 mg/L)

The plates containing the biofilms were washed twice with a PBS buffer then incubated for 30 minutes in the dark in 200 µL of resazurin (10 m/ml) in each well. Resazurin (7-Hydroxy-3H-phenoxazin-3-on 10-oxide) is a blue-coloured non-toxic dye which can spread in bacteria and then be reduced to resorufin, a fluorescent compound. The viability of the bacteria was thus measured by following the development of the fluorescence of the resorufin which is directly proportional to the number of viable bacteria in the medium.

The measurement was conventionally measured by spectrophotometry (length of excitation wavelength at 560 nm and transmission at 590 nm) with a spectramax M4. The results obtained are presented in FIGS. 9 and 10*a* to 10*c*.

FIG. 9 illustrates the viability (% of viability with respect to the control—non-treated) of the bacteria of an isolate of *S. aureus* Sa2003/1083 (isolated from a knee prosthesis) having developed a biofilm, following contact with ciprofloxacin at Cmin concentration as an antibiotic in combination with DNase as the sole enzyme or with mannanase (Ma)

as the sole enzyme or with DNase and mannanase (Ma) as enzymes or with Dispersin B (DspB), DNase and cellulase (Ce) as enzymes (DCC).

FIGS. 10a to 10c illustrate the viability (% of viability with respect to the control) of the bacteria of an isolate of *K. pneumoniae* Kp826 (isolated from a central venous catheter) having developed a biofilm, following contact with
  (A) ciprofloxacin at Cmin concentration as an antibiotic in combination with DNase as the sole enzyme or with cellulase (Ce) as the sole enzyme or with DNase and cellulase (Ce) as enzymes or with Dispersin B (DspB), DNase and cellulase (Ce) as enzymes (DCC);
  (B) amikacin at Cmin concentration as an antibiotic in combination with Dispersin B (DspB) as the sole enzyme or with cellulase (Ce) as the sole enzyme or with Dispersin B (DspB) and cellulase (Ce) as enzymes or with Dispersin B (DspB), DNase and cellulase (Ce) as enzymes (DCC);
  (C) tobramycin at Cmin concentration as an antibiotic in combination with Dispersin B (DspB) as the sole enzyme or with cellulase (Ce) as the sole enzyme or with Dispersin B (DspB) and cellulase (Ce) as enzymes or with Dispersin B (DspB), DNase and cellulase (Ce) as enzymes (DCC).

In the graphs of FIGS. 9a to 9c the results of a statistical test are shown (One-way ANOVA with multiple comparison Dunnett's test) carried out in order to determine if a significant difference can be observed between the Cmax of the antibiotic and the Cmin of the antibiotic associated with one or several enzymes. The characters *,  and * respectively mean $p<0.05$, $p<0.01$ and $p<0.001$.

From these graphs, it can be observed that all the combinations [antibiotic at Cmin+enzyme(s)] tested allow the viability of the bacteria of the *S. aureus* Sa2003/1083 species and the *K. pneumoniae* Kp862 species to be reduced in a significant manner (p value at least less than 0.05) in comparison to the sole antibiotic at a concentration of Cmax. Similarly, it can be noted that a significant difference is observed between all the combinations [antibiotic at Cmin+enzyme(s)] tested and the control (non-treated biofilm), which is not the case for a comparison between the effect of the antibiotic alone (at Cmin or Cmax) and the control (non-treated biofilm).

This shows the advantage of combining an antibiotic and at least one enzyme for the preventative and/or curative treatment of post-implantation infections at an infection site, said infections being post-implantation infections.

B. Cytotoxicity

Figure 11B:
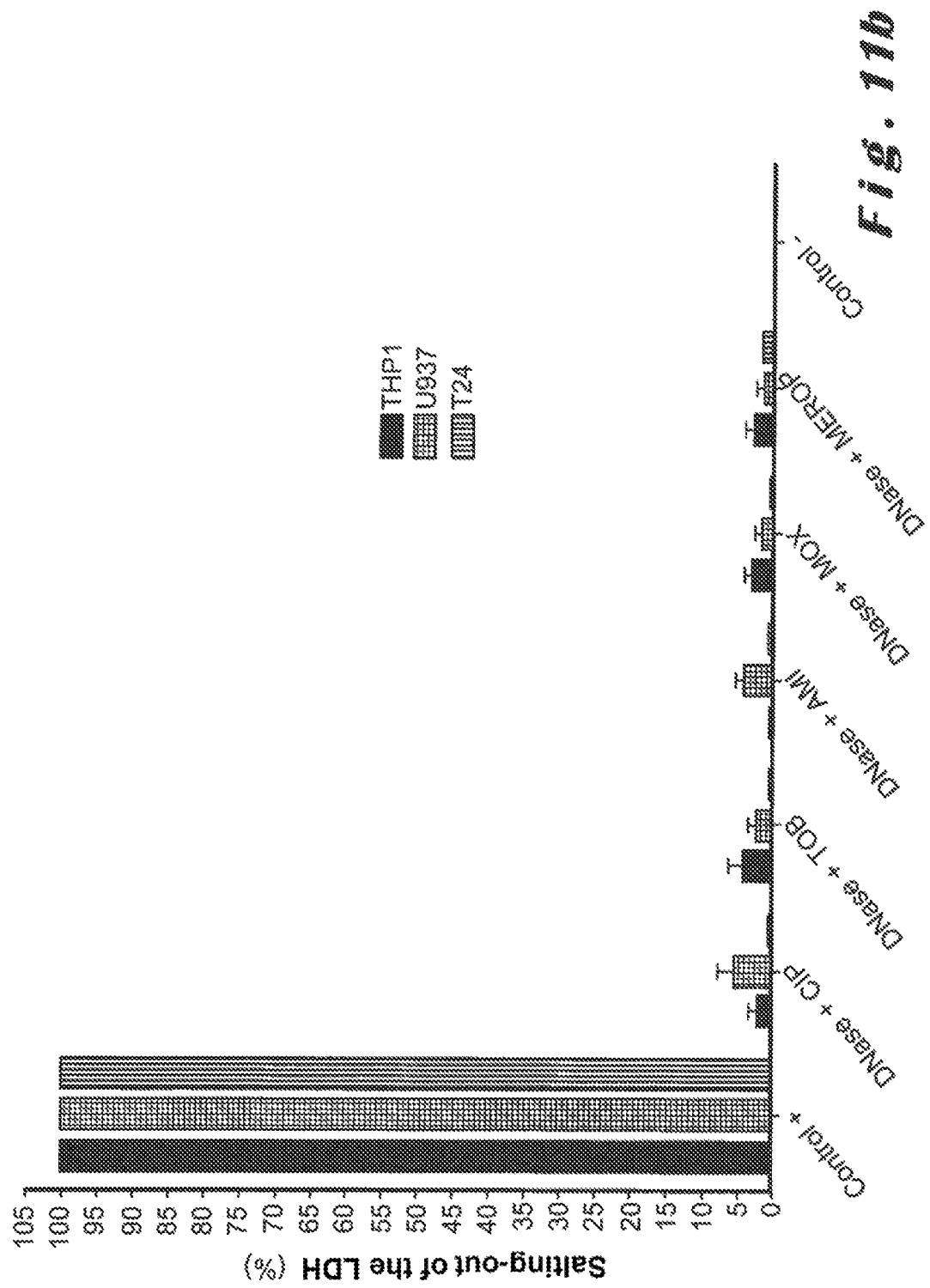
Figure 11C:
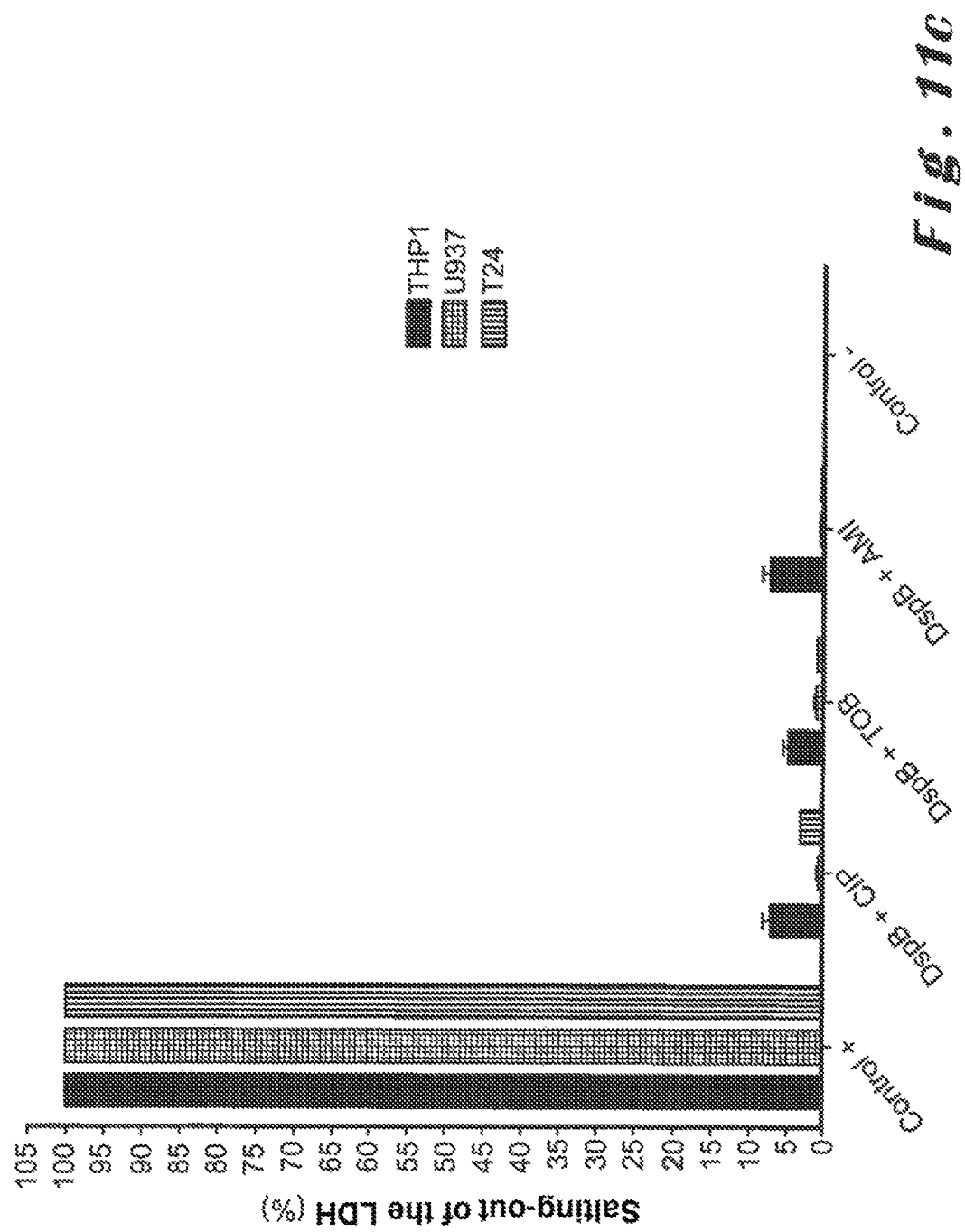
Figure 11C:
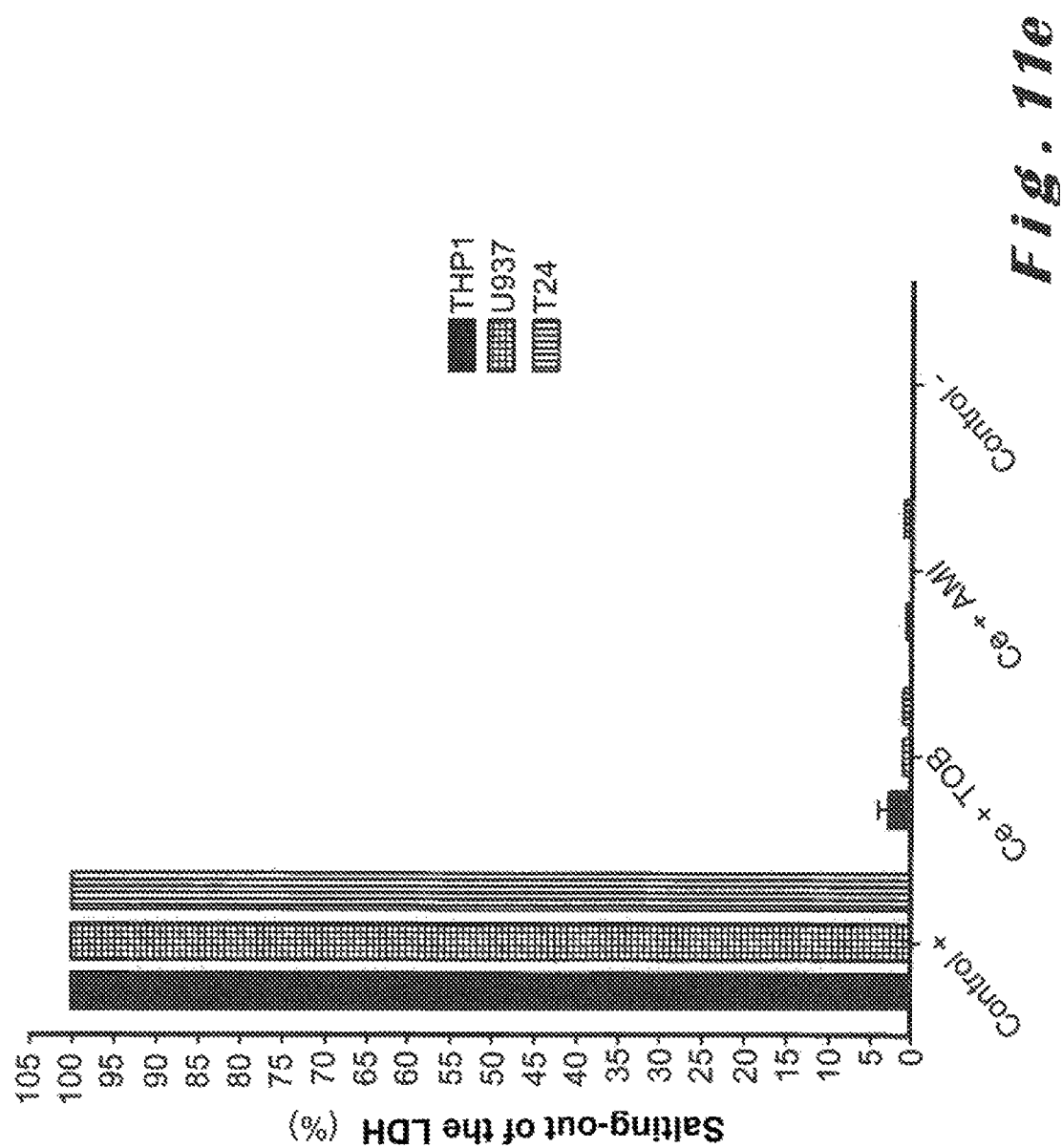
Figure 11F:
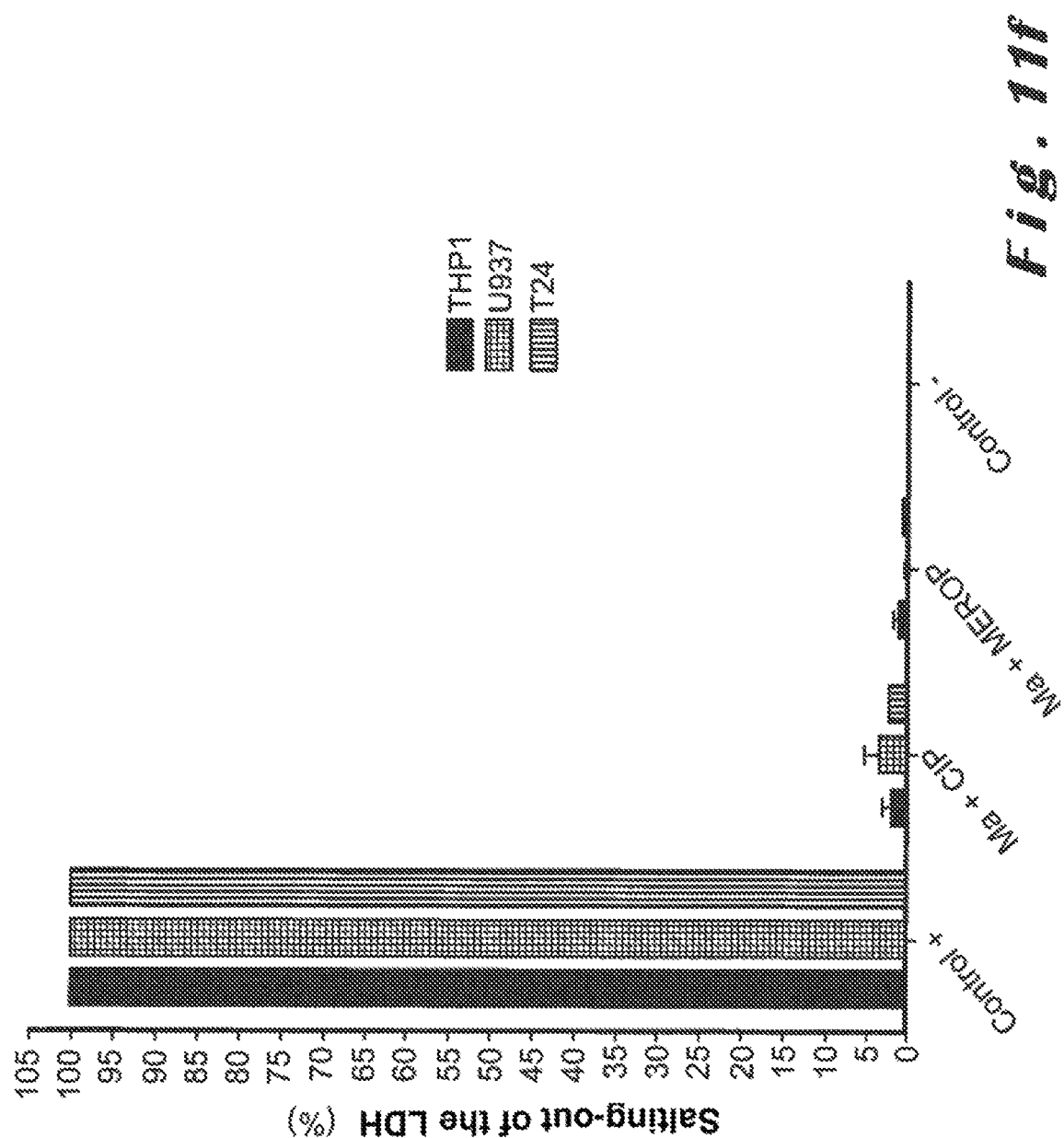

A protocol identical to that described under point B of Example 1 was carried out in order to judge the cytotoxicity of different combinations of an antibiotic and an enzyme on the human cell lines THP1, U937 and T24. The results obtained are presented in FIGS. 11a to 11f. In these graphs, the negative control allows the activity of the LDH released by the normal non-treated cells (spontaneous release LDH) to be determined and the positive control allows the maximum activity of the LDH released by treated cells to be determined with a cell lysis solution. To conducts these tests, the following concentrations were observed:
  enzymes: 0.05%; DCC=0.025% DNase+0.01% Dispersin B (DspB)+0.05% cellulase (Ce)
  amikacin: Cmin=5 mg/L
  tobramycin: Cmin=0.9 mg/L
  moxifloxacin: Cmin=0.3 mg/L
  meropenem: Cmin=0.1 mg/L
  ciprofloxacin: Cmin=0.6 mg/L FIG. 11a illustrates the salting-out of the LDH (%) of the human cell lines THP1, U937 and T24 for savinase (Sav) in combination with the antibiotic ciprofloxacin (CIP) or the antibiotic tobramycin (TOB) or the antibiotic amikacin (AMI) or the antibiotic moxifloxacin (MOX). FIG. 11b illustrates the salting-out of the LDH (%) of the human cell lines THP1, U937 and T24 for DNase in combination with the antibiotic ciprofloxacin (CIP) or the antibiotic tobramycin (TOB) or the antibiotic amikacin (AMI) or the antibiotic moxifloxacin (MOX) or the antibiotic meropenem (MEROP). FIG. 11c illustrates the salting-out of the LDH (%) of the human cell lines THP1, U937 and T24 for Dispersin B (DspB) in combination with the antibiotic ciprofloxacin (CIP) or the antibiotic tobramycin (TOB) or the antibiotic amikacin (AMI). FIG. 11d illustrates the salting-out of the LDH (%) of the human cell lines THP1, U937 and T24 for lipase (Li) in combination with the antibiotic ciprofloxacin (CIP) or the antibiotic amikacin (AMI). FIG. 11e illustrates the salting-out of the LDH (%) of the human cell lines THP1, U937 and T24 for cellulase (Ce) in combination with the antibiotic tobramycin (TOB) or the antibiotic amikacin (AMI). FIG. 11f illustrates the salting-out of the LDH (%) of the human cell lines THP1, U937 and T24 for mannanase (Ma) in combination with the antibiotic ciprofloxacin (CIP) or the antibiotic meropenem (MEROP).

From these graphs in FIGS. 11a to 11f, it can be concluded that none of the combinations (antibiotic+enzyme) show any toxicity for the human cell lines tested.

C. Conclusion from Example 2

From Example 2, it is very clear that the present invention is not limited to a particular composition such as that of Example 1, but rather that a whole range of different combinations and thus different compositions according to the invention are effective in the treatment of post-implantation infections. Furthermore, it was shown that the compositions according to the invention are not cytotoxic.

It is understood that the present invention is in no way limited to the embodiments described above and that modifications may be made without departing from the scope of the appended claims.

The invention claimed is:
1. A method of treatment for post-implantation infections of mammalian bodies, the method comprising:
  administering a therapeutically effective amount of a composition comprising a combination of an enzymatic cocktail of Dispersin B, cellulase, and DNase; and a fluoroquinolone microbicidal molecule, wherein the composition is sterile, and wherein the composition is effective to reduce by at least 1 Log 10 the number of viable bacteria in biofilms formed post-implantation by bacteria species selected from the species group consisting of *Staphylococcus aureus* to a mammalian body following implantation of an implantable medical device, the mammalian body being subject to post-implantation infection by bacteria belonging to the species *Staphylococcus aureus*.

* * * * *